(12) United States Patent
Agulnick et al.

(10) Patent No.: US 7,695,963 B2
(45) Date of Patent: Apr. 13, 2010

(54) METHODS FOR INCREASING DEFINITIVE ENDODERM PRODUCTION

(75) Inventors: Alan Agulnick, San Diego, CA (US); Kevin D'Amour, San Diego, CA (US); Emmanuel Edward Baetge, Encinitas, CA (US)

(73) Assignee: Cythera, Inc., San Diego, CA (US)

( * ) Notice: Subject to any disclaimer, the term of this patent is extended or adjusted under 35 U.S.C. 154(b) by 133 days.

(21) Appl. No.: 11/860,494

(22) Filed: Sep. 24, 2007

(65) Prior Publication Data

US 2009/0093372 A1 Apr. 9, 2009

(51) Int. Cl.
C12N 5/071 (2010.01)
C12N 5/00 (2006.01)
C12N 5/02 (2006.01)
C12N 5/07 (2010.01)
C12N 5/10 (2006.01)

(52) U.S. Cl. .................. 435/366; 435/325; 435/363; 435/375

(58) Field of Classification Search .................. 435/366
See application file for complete search history.

(56) References Cited

U.S. PATENT DOCUMENTS

| | | | |
|---|---|---|---|
| 5,453,357 A | 9/1995 | Hogan | |
| 5,670,372 A | 9/1997 | Hogan | |
| 5,690,926 A | 11/1997 | Hogan | |
| 5,817,637 A | 10/1998 | Weiner et al. | |
| 5,830,876 A | 11/1998 | Weiner et al. | |
| 5,843,780 A | 12/1998 | Thomson | |
| 6,015,671 A | 1/2000 | Field | |
| 6,090,622 A | 7/2000 | Gearhart et al. | |
| 6,165,993 A | 12/2000 | Herrmann et al. | |
| 6,200,806 B1 | 3/2001 | Thomson | |
| 6,251,671 B1 | 6/2001 | Hogan et al. | |
| 6,261,281 B1 | 7/2001 | Mathiesen et al. | |
| 6,458,589 B1 | 10/2002 | Rambhatla et al. | |
| 6,506,574 B1 | 1/2003 | Rambhatla et al. | |
| 6,872,389 B1 | 3/2005 | Faris | |
| 6,921,811 B2 | 7/2005 | Zamora et al. | |
| 7,033,831 B2 | 4/2006 | Fisk et al. | |
| 7,153,684 B1 | 12/2006 | Hogan | |
| 7,256,042 B2 | 8/2007 | Rambhatla et al. | |
| 7,326,572 B2 | 2/2008 | Fisk et al. | |
| 2002/0072117 A1 | 6/2002 | Xu et al. | |
| 2002/0090723 A1 | 7/2002 | Carpenter et al. | |
| 2003/0138948 A1 | 7/2003 | Fisk et al. | |
| 2003/0138949 A1 | 7/2003 | Bhushan et al. | |
| 2003/0175956 A1 | 9/2003 | Bodnar et al. | |
| 2003/0190748 A1 | 10/2003 | Thomson | |
| 2003/0224411 A1 | 12/2003 | Stanton et al. | |
| 2004/0127406 A1 | 7/2004 | Presnell et al. | |
| 2004/0229350 A1 | 11/2004 | Strelchenko et al. | |
| 2005/0079159 A1 | 4/2005 | Shastri et al. | |
| 2006/0003446 A1 | 1/2006 | Keller et al. | |
| 2006/0019387 A1 | 1/2006 | Faris | |
| 2006/0040385 A1 | 2/2006 | Itskovitz-Eldor et al. | |
| 2006/0040387 A1 | 2/2006 | Fisk et al. | |
| 2006/0128018 A1 | 6/2006 | Zwaka et al. | |
| 2006/0148081 A1 | 7/2006 | Kelly et al. | |
| 2006/0276420 A1 | 12/2006 | Keller et al. | |
| 2007/0154984 A1 * | 7/2007 | D'Amour et al. | .......... 435/69.1 |
| 2007/0281355 A1 | 12/2007 | Dalton et al. | |

FOREIGN PATENT DOCUMENTS

| | | |
|---|---|---|
| EP | 1298201 A | 4/2003 |
| EP | 1627912 A | 2/2006 |
| WO | WO 98/30679 | 7/1998 |
| WO | WO 99/13915 | 3/1999 |
| WO | WO 00/29442 | 5/2000 |
| WO | WO 02/10347 | 2/2002 |
| WO | WO 02/34880 | 5/2002 |
| WO | WO 02/059278 | 8/2002 |
| WO | WO 03/050249 A2 | 6/2003 |
| WO | WO 03/050249 A3 | 6/2003 |
| WO | WO 03/100026 | 12/2003 |
| WO | WO 2004/098490 | 11/2004 |
| WO | WO 2005/017131 | 2/2005 |
| WO | WO 2005/033294 | 4/2005 |
| WO | WO 2005/045001 | 5/2005 |
| WO | WO 2005/063971 | 7/2005 |
| WO | WO 2005063971 A2 * | 7/2005 |
| WO | WO 2005/097980 A2 | 10/2005 |
| WO | WO 2005/116073 | 12/2005 |
| WO | WO 2006/016999 | 2/2006 |
| WO | WO 2006/017134 | 2/2006 |
| WO | WO 2006/020919 A2 | 2/2006 |
| WO | WO 2006/034873 | 4/2006 |

(Continued)

OTHER PUBLICATIONS

Dang, 2004, Stem Cells, 22:75-282.*

(Continued)

Primary Examiner—Valarie Bertoglio
(74) Attorney, Agent, or Firm—Knobbe, Martens, Olson & Bear LLP

(57) ABSTRACT

Disclosed herein are methods for increasing the production of definitive endoderm cells from pluripotent stem cells. Also disclosed herein are agents capable of increasing definitive endoderm cell production.

20 Claims, 5 Drawing Sheets

FOREIGN PATENT DOCUMENTS

| WO | WO 2006/083782 | 8/2006 |
|---|---|---|
| WO | WO 2007/002210 A2 | 1/2007 |
| WO | WO 2007/088372 | 8/2007 |

OTHER PUBLICATIONS

Valdimarsdottir et al., Functions of the TGFb superfamily in human embryonic stem cells. APMIS, 113(11-12):773-89, 2005.*

Abe, et al., "Endoderm-Specific Gene Expression in Embryonic Stem Cells Differentiated to Embryoid Bodies," *Experimental Cell Research*. (1996) 229(1): 27-34.

Alexander, J., and Stainier, D. Y., "A Molecular Pathway Leading to Endoderm Formation in Zebrafish" *Curr Biol* (1999) 9: 1147-1157.

Alexander, et al., "Casanova Plays an Early and Essential Role in Endoderm Formation in Zebrafish" *Dev Biol* (1999) 215: 343-357.

Ang, et al., "HNF-3β is Essential for Node and Notochord Formation in Mouse Development" *Cell* (1994) 78: 561-574.

Ang, et al. "The Formation and Maintenance of the Definitive Endoderm Lineage in the Mouse: Involvement of HNF3/Forkhead Proteins" *Development* (1993) 119: 1301-1315.

Aoki, et al., "Regulation of Nodal Signalling and Mesendoderm Formation by TARAM-A, A Tgfbeta-Related Type I Receptor" *Dev Biol* (2002) 241: 273-288.

Arnold, et al., "*Brachyury* is a Target Gene of the Wnt/β-catenin Signaling Pathway" *Mech. Dev.* (2000) 91: 249-258.

Assady et al. "Insulin Production by Human Embryonic Stem Cells" *Diabetes* (2001) 50(8): 1691-1697.

Bachiller, et al., The Organizer Factors Chordin and Noggin are Required for Mouse Forebrain Development *Nature* (2000) 403: 658-661.

Bain, et al., "Embryonic Stem Cells Express Neuronal Properties in Vitro." *Developmental Biology* (1995) 168: 342-357.

Barbacci, et al., "Variant Hepatocyte Nuclear Factor 1 is Required for Visceral Endoderm Specification" *Development* (1999) 126: 4795-4805.

Barry, et al., "The Production of Monoclonal Antibodies by Genetic Immunization" *Biotechniques* (1994) 16: 616-620.

Batlle, et al., The Transcription Factor Snail is a Repressor of *E-cadherin* Gene Expression in Epithelial Tumour Cells *Nat Cell Biol* (2000) 2: 84-89.

Beck, et al., "Extra-Embryonic Proteases Regulate Nodal Signalling During Gastrulation" *Nat Cell Biol* (2002) 4: 981-985.

Beddington, et al. "Brachyury—A Gene Affecting Mouse Gastrulation and Early Organogenesis" *Dev Suppl*, (1992) 157-165.

Bendall, et al. "IGF and FGF Cooperatively Establish Regulatory Stem Cell Niche of Pluripotent Human Cells In Vitro." Nature (2007), 448; 1015-1021.

Blum, et al., Gastrulation in the Mouse: The Role of the Homeobox Gene *goosecoid* *Cell* (1992) 69: 1097-1106.

Bongso, et al., "Isolation and Culture of Inner Cell Mass Cells From Human Blastocysts" *Hum Reprod* (1994) 9: 2110-2117.

Bost, et al., "Retinoic Acid Activation of the ERK Pathway is Required for Embryonic Stem Cell Commitment into the Adipocyte Lineage." *Biochem. J.* (2002) 361: 621-627.

Brennan, et al., "*Nodal* Signalling in the Epiblast Patterns the Early Mouse Embryo" *Nature* (2001) 411: 965-969.

Candia, et al., Differential Localization of Mox-1 and Mox-2 Proteins Indicates Distinct Roles During Development *Int J Dev Biol* (1996) 40: 1179-1184.

Candia, et al., "*Mox-1* and *Mox-2* Define a Novel Homeobox Gene Subfamily and are Differentially Expressed During Early Mesodermal Patterning in Mouse Embryos" *Development* (1992) 116: 1123-1136.

Cereghini, et al. "Expression Patterns of vHNF1 and HNF1 Homeoproteins in Early Postimplantation Embryos Suggest Distinct and Sequential Developmental Roles" *Development* (1992) 116: 783-797.

Chang, et al., "Genetic Analysis of the Mammalian Transforming Growth Factor-Beta Superfamily" *Endocr Rev* (2002) 23: 787-823.

Chen, et al., "Retinoic Acid Signaling is Essential for Pancreas Development and Promotes Endocrine at the Expense of Exocrine Cell Differentiation in *Xenopus*" *Developmental Biology* (2004) 271: 144-160.

Ciani, et al., "WNTS in the Vertebrate Nervous System: From Patterning to Neuronal Connectivity" *Nature Reviews/Neuroscience* (2005) 6: 351-382.

Ciruna, et al., "FGF Signaling Regulates Mesoderm Cell Fate Specification and Morphogenetic Movement at the Primitive Streak" *Day Cell* (2001) 1: 37-49.

Ciruna, et al., "Chimeric Analysis of *Fibroblast Growth Factor Receptor-1 (Fgfr1)* Function: A Role for FGFR1 in Morphogenetic Movement Through the Primitive Streak" *Development* (1997) 124: 2829-2841.

Collombat, et al., "Specifying Pancreatic Endocrine Cell Fates" *Mech. Dev.* (2006) 123(7): 501-512.

Conley, et al. "BMPs Regulate Differentiation of a Putative Visceral Endoderm Layer Within Human Embryonic Stem-Cell-Derived Embryoid Bodies" *Biochem Cell Biol* (2007) 85: 121-132.

Conlon, et al., "A primary requirement for nodal in the formation and maintenance of the primitive streak in the mouse" *Development* (1994) 120: 1919-1928.

Costaglia, et al., "Genetic Immunization Against the Human Thyrotropin Receptor Causes Thyroiditis and Allows Production of Monoclonal Antibodies Recognizing the Native Receptor" *J. Immunol.* (1998) 160: 1458-1465.

Czyz et al. "Embryonic Stem Cell Differentiation: The Role of Extracellular Factors" *Differentiation* (2001) 68(4-5): 167-174.

Daheron et al. "LIF/STAT3 Signaling Fails to Maintain Self-Renewal of Human Embryonic Stem Cells" *Stem Cells* (2004) 22: 770-778.

D'Amour et al. "Production of Pancreatic Hormone-Expressing Endocrine Cells From Human Embryonic Stem Cells" *Nature Biotechnology* (2006) 24: 1392-1401.

D'Amour, et al., "Efficient Differentiation of Human Embryonic Stem Cells to Definitive Endoderm" *Nature Biotechnology* (2005) 23(12): 1534-1541.

Dang, et al., "Controlled, Scalable Embryonic Stem Cell Differentiation Culture" *Stem Cells* (2004) 22: 275-282.

Dani, et al., "Differentiation of Embryonic Stem Cells into Adipocytes in Vitro." *J. Cell Science* (1997) 110: 1279-1285.

Database UniProt, "1-acyl-sn-glycerol-3-phosphate acyltransferase gmma (EC 2.3.1.51) (1-AGP acyltransferase 3) (1-AGPAT 3) (Lysophosphatidic acid acyltransfearse gamma) (LPAAT-gamma) (1-acylglycerol-3-phosphate 0-acyltransfearse 3)" retrieved from EBI accession No. UNIPROT: Q9NRZ7 on Oct. 1, 2000.

de Caestecker, M. "The Transforming Growth Factor-β Superfamily of Receptors" *Cytokine & Growth Factor Rev.* (2004) 15: 1-11.

de Felice, et al., "TTF-1 Phosphorylation is Required for Peripheral Lung Morphogenesis, Perinatal Survival, and Tissue-Specific Gene Expression" *J. Biological Chemistry* (2003) 278(37): 35574-35583.

Dougan, et al., "The Role of the Zebrafish Nodal-Related Genes Squint and Cyclops in Patterning of Mesendoderm" *Development* (2003) 130: 1837-1851.

Dudas, et al., "The Homebox Transcription Factor Prox1 is Highly Conserved in Embryonic Hepatoblasts and in Adult and Transformed Hepatocytes, but is Absent from Bile Duct Epithelium" *Anat Embryol* (2004) 208: 359-366.

Edlund, H., "Factors Controlling Pancreatic Cell Differentiation and Function," *Diabetologia* (2001) 44(9): 1071-1079.

Elms, et al., "Overlapping and Distinct Expression Domains of *Zic2* and *Zic3* During Mouse Gastrulation" *Gene Expression Patterns* (2004) 4: 505-511.

Falasca, et al., "Retinoic Acid Treatment Induces Apoptosis or Expression of a More Differentiated Phenotype on Different Fractions of Cultured Fetal Rat Hepatocytes" *Hepatology* (1998) 28(3): 727-737.

Fehling, et al., "Development and Disease: Tracking Mesoderm Induction and its Specification to the Hemangioblast during Embryonic Stem Cell Differentiation" *Development* (2003) 130: 4217-4227.

Feldman, et al., "Zebrafish Organizer Development and Germ-Layer Formation Require Nodal-Related Signals" *Nature* (1998) 395: 181-185.

Feng, et al., "HIV-1 Entry Cofactor: Functional Cdna Cloning of a Seven-Transmembrane, G Protein-Coupled Receptor" *Science* (1996) 272: 872-877.

Freund, et al. "Insulin Redirect Differentiation from Cardiogenic Mesoderm and Endoderm to Neuroectoderm in Differentiating Human Embryonic Stem Cells." Stem Cells (2007), published online Dec. 20, 2007.

Futaki, et al., "Molecular Basis of Constitutive Production of Basement Membrane Components: Gene Expression Profiles of Engelbreth-Holm-Swarm Tumor and F9 Embryonal Carcinoma Cells" *J Biol Chem.* (2003) 278(50): 50691-50701.

Gardner, Robert L., "Stem Cells and Regenerative Medicine: Principles, Prospects and Problems" *C. R. Biologies* (2007) 330: 465-473.

Goumans, et al., "Mouse Embryonic Stem Cells with Aberrant Transforming Growth Factor B signaling Exhibit Impaired Differentiation in Vitro and in Vivo" *Differentiation* (1998) 63: 103-113.

Grapin-Botton, A., and Melton, D. A., "Endoderm Development: From Patterning to Organogenesis" *Trends Genet* (2000) 16: 124-130.

Haegel, et al., "Lack of β-catenin Affects Mouse Development at Gastrulation" *Development* (1995) 121: 3529-3537.

Hallonet, et al., "Maintenance of the Specification of the Anterior Definitive Endoderm and Forebrain Depends on the Axial Mesendoderm: A Study Using *HNF3β/Foxa2* Conditional Mutants" *Dev Biol* (2002) 243: 20-33.

Hamazaki, et al., "Hepatic Maturation in Differentiating Embryonic Stem Cells in Vitro" *FEBS Letter* (2001) 497(1): 15-19.

Hansson, et al., "Artifactual Insulin Release from Differentiated Embryonic Stem Cells" *Diabetes* (2004) 53: 2603-2609.

Harris, T. M., and Childs, G., "Global Gene Expression Patterns During Differentiation of F9 Embryonal Carcinoma Cells Into Parietal Endoderm" *Funct Integr Genomics* (2002) 2: 105-119.

Harrison, et al., "Pancreas Dorsal Lobe Agenesis and Abnormal Islets of Langerhans in *Hlxb9*-deficient Mice" *Nature Genetics* (1999) 23: 71-75.

Haumaitre, et al. "Functions of HNF1 Family Members in Differentiation of the Visceral Endoderm Cell Lineage" *J. Biol. Chem.* (2003) 278(42): 40933-40942.

Henry, et al., "*Mixer*, a Homeobox Gene Required for Endoderm Development" *Science* (1998) 281: 91-96.

Herrmann, et al., "Cloning of the *T* Gene Required in Mesoderm Formation in the Mouse" *Nature* (1990) 343: 617-622.

Hogan, B. L., "Bone Morphogenetic Proteins in Development" *Curr Opin Genet Dev* (1996) 6: 432-438.

Holland, et al., "Experimental Control of Pancreatic Development and Maintenance" *Proc Natl Acad Sci USA* (2002) 99(19): 12 236-12 241.

Houard, et al., "HNF-6-Independent Differentiation of Mouse Embryonic Stem Cells into Insulin-Producing Cells" *Diabetologia* (2003) 46: 378-385.

Houde, et al., "Intestinal Epithelial Cell Differentiation Involves Activation of p38 Mitogen-activated Protein Kinase that Regulates the Homeobox Transcription Factor CDX2" *J. Biological Chemistry* (2001) 276(24): 21885-21894.

Howe, et al., "Expression of SPARC/Osteonectin Transcript in Murine Embryos and Gonads" *Differentiation* (1998) 37: 20-25.

Hudson, et al., "Xsox17alpha and -beta Mediate Endoderm Formation in Xenopus" *Cell* (1997) 91: 397-405.

Huelsken, et al., "Requirement for β-Catenin in Anterior-Posterior Axis Formation in Mice" *J Cell Biol* (2000) 148: 567-578.

Humphrey, et al. "Maintenance of Pluripotency in Human Embryonic Stem Cells is STAT3 Independent" *Stem Cells* (2004) 22: 522-530.

Imada, et al., "Fetomodulin: Marker Surface Protein of Fetal Development Which is Modulatable by Cyclic AMP" *Dev Biol* (1987)122: 483-491.

Jain, et al., "Glucose Control and Long-Term Survival in Breeding/Worcester Rats After Intraperitoneal Implantation of Hydrophilic Macrobeads containing Porcine Islets without Immunosuppression" *Transplantation* (1999) 68(11): 1693-1700.

Jonsson, J., et al., "Insulin-promoter-factor 1 is required for pancreas development n mice", Nature, vol. 371, pp. 606-609, (1994).

Jones, et al., "Differences Between Human and Mouse Alpha-Fetoprotein Expression During Early Development" *J. Anat.* (2001) 198: 555-559.

Kahan, et al., "Pancreatic Precursors and Differentiated Islet Cell Types from Murine Embryonic Stem Cells: An In Vitro Model to Study Islet Differentiation" *Diabetes* (2003) 52(8): 2016-2024.

Kalinichenko, et al., "The Forkhead Box F1 Transcription Factor is Expressed in Brain and Head Mesenchyme During Mouse Embryonic Development" *Gene Expr Patterns* (2003) 3: 153-158.

Kanai-Azuma, et al., "Depletion of Definitive Gut Endoderm in Sox17-Null Mutant Mice" *Development* (2002) 129: 2367-2379.

Katoh, M., "Expression of Human SOX7 in Normal Tissues and Tumors" *Int J Mol Med* (2002) 9: 363-368.

Kawahira, et al., "Hedgehog Signaling Regulates Expansion of Pancreatic Epithelial Cells" *Developmental Biology* (2005) 280: 111-121.

Kawaji, et al., "Exploration of Novel Motifs Derived from Mouse cDNA Sequences" *Genome Research* (2002) 12: 367-378.

Keller, G.M., "In Vitro Differentiation of Embryonic Stem Cells" *Curr Op Cell Biol* (1995) 7: 862-896.

Khoo, et al., "Growth and Differentiation of Embryoid Bodies Derived from Human Embryonic Stem Cells: Effect of Glucose and Basic Fibroblast Growth Factor", *Biology of Reproduction* (2005) 73: 1147-1156.

Kieffer, T.J., and J.F. Habener, "The Glucagon-Like Peptides" *Endocrinology Reviews* (1999) 20(6): 876-913.

Kikuchi, et al., "Casanova Encodes a Novel Sox-Related Protein Necessary and Sufficient for Early Endoderm Formation in Zebrafish" *Genes Dev* (2001) 15: 1493-1505.

Kilpatrick, et al., "Gene Gun Delivered DNA-Based Immunizations Mediate Rapid Production of Murine Monoclonal Antibodies to the Flt-3 Receptor" *Hybridoma* (1998) 17: 569-576.

Kim, C. H., and Broxmeyer, H. E., "Chemokines: Signal Lamps for Trafficking of T and B Cells for Development and Effector Function" *J Leukoc Biol* (1999) 65: 6-15.

Kimelman, D., and Griffin, K. J., "Vertebrate Mesendoderm Induction and Patterning" *Curr Opin Genet Dev* (2000)10: 350-356.

Kinder, et al., "The Organizer of the Mouse Gastrula is Composed of a Dynamic Population of Progenitor Cells for the Axial Mesoderm" *Development* (2001) 128: 3623-3634.

Krasemann, et al., "Generation of Monoclonal Antibodies Against Proteins With an Unconventional Nucleic Acid-Based Immunization Strategy" *J. Biotechnol.* (1999) 73: 119-129.

Kubo, et al., "Development of definitive endoderm from embryonic stem cells in culture" *Development* (2004)131: 1651-1662.

Kumar, et al., "Nodal Signaling Uses Activin and Transforming Growth Factor-Beta Receptor-Regulated Smads" *J Biol Chem* (2001) 276: 656-661.

Kuo, et al., "Role of Histone Acetyltransferases and Deacetylases in Gene Regulation" *BioEssays* (1998) 20(8): 615-626.

Labosky, et al., "Embryonic Germ Cell Lines and Their Derivation From Mouse Primordial Germ Cells" *Ciba Found Symp* (1994) 182: 157-168; discussion: 168-178.

Labosky, et al., "Mouse Embryonic Germ (EG) Cell Lines: Transmission Through the Germline and Differences in the Methylation Imprint of Insulin-Like Growth Factor 2 Receptor (Igf2r) Gene Compared With Embryonic Stem (ES) Cell Lines" *Development* (1994) 120: 3197-3204.

Latif, et al., "A Simple Method of Staining Fresh and Cultured Islets," *Transplantation* (1998) 45(4): 827-830.

Lawson, et al., "*Bmp4* is Required for the Generation of Primordial Germ Cells in the Mouse Embryo" *Genes Dev* (1999) 13: 424-436.

Li, et al., "Selective Agenesis of the Dorsal Pancreas in Mice Lacking Homeobox Gene *Hlxb9*" *Nature Genetics* (1999) 23: 67-70.

Lickert, et al., "Formation of Multiple Hearts in Mice Following Deletion of Beta-Catenin in the Embryonic Endoderm" *Dev Cell* (2002) 3: 171-181.

Liu, et al., "Requirement for *Wnt3* in Vertebrate Axis Formation" *Nat Genet* (1999) 22: 361-365.

Loebel, et al., "A Gut Feeling" *Nat. Biotechnol.* (2005) 23(12): 1491-1492.

Lowe, et al., "Genetic Dissection of *Nodal* Function in Patterning the Mouse Embryo" *Development* (2001) 128: 1831-1843.

Lu, et al., "From Fertilization to Gastrulation: Axis Formation in the Mouse Embryo" *Curr Opin Genet Dev* (2001) 11: 384-392.

Lumelsky, et al., "Differentiation of Embryonic Stem Cells to Insulin-Secreting Structures Similar to Pancreatic Islets" *Science* (2001) 292: 1389-1394.

Ma, et al., "The chemokine receptor CXCR4 is required for the retention of B lineage and granulocytic precursors within the bone marrow microenvironment" *Immunity* (1999)10: 463-471.

Martin, et al., "Dorsal Pancreas Agenesis in Retinoic Acid-Deficient *Raldh2* Mutant Mice" *Developmental Biology* (2005) 284: 399-411.

Maruoka, et al., "Comparison of the Expression of Three Highly Related Genes, *Fgf8, Fgf17* and *Fgf18*, in the Mouse Embryo" *Mech Dev* (1998) 74: 175-177.

Matsuda T, et al. "STAT3 Activation is Sufficient to Maintain an Undifferentiated State of Mouse Embryonic Stem Cells" (Aug. 2, 1999) EMBO J, 18(15):4261-9.

McGrath, et al., "Expression of Homeobox Genes, Including and Insulin Promoting Factor, in the Murine Yolk Sac at the Time of Hematopoietic Initiation" *Mol Reprod Dev* (1997) 48: 145-153.

McGrath, et al., "Embryonic Expression and Function of the Chemokine SDF-1 and Its Receptor, CXCR4" *Dev Biol.* (1999) 213: 442-456.

McLean, et al., "Activin A Efficiently Specifies Definitive Endoderm from Human Embryonic Stem Cells Only When Phosphtidylinositol 3-Kinase Signaling Is Suppressed" *Stem Cells* (2007) 25: 29-38.

Micallef, et al., "Retinoic Acid Induces Pdx1-positive Endoderm in Differentiating Mouse Embryonic Stem Cells" *Diabetes* (2005) 54(2): 301-305.

Millonig et al., "Molecular Analysis of the Distal Enhancer of the Mouse Alpha-Fetoprotein Gene" *Mol. Cell Biol.* (1995) 15: 3848-3856.

Milne, et al. "Generation of Insulin-Expressing Cells from Mouse Embryonic Stem Cells" *Biochemical and Biophysical Research Communications* (2005) 328: 399-403.

Miyazono, et al., "Divergence and Convergence of TGF-beta/BMP Signaling" *J Cell Physiol* (2001)187: 265-276.

Mizusawa, et al., "Differentiation Phenotypes of Pancreatic Islet Beta- and Alpha-Cells are Closely Related with Homeotic Genes and a Group of Defferentially Expressed Genes" *Gene: An Int. Journal on Genes and Genomes* (2004) 331: 53-63.

Molotkov, et al., "Retinoic Acid Generated by *Raldh2* in Mesoderm Is Required for Mouse Dorsal Endodermal Pancreas Development" *Developmental Dynamics* (2005) 232: 950-957.

Moriya, et al., "In Vitro Pancreas Formation from Xenopus Ectoderm Treated with Activin and Retinoic Acid" *Develop. Growth Differ.* (2000) 42: 593-602.

Nagai, et al., "The Expression of the Mouse *Zic1, Zic2*, and *Zic3* Gene Suggests an Essential Role for *Zic* Genes in Body Pattern Formation" *Dev Biol* (1997) 182: 299-313.

Nagasawa, et al., "Defects of B-cell Lymphopoiesis and Bone-Marrow Myelopoiesis in Mice Lacking the CXC Chemokine PBSF/SDF-1" *Nature* (1996) 382: 635-638.

Nakagawa, et al., "Recruitment and Activation of Rac1 by the Formation of E-cadherin-mediated Cell-cell Adhesion Sites" *J. Cell Science* (2001) 114(10): 1829-1838.

Nieto, M.A., The Snail Superfamily of Zinc-Finger Transcription Factors *Nat Rev Mol Cell Biol* (2002) 3: 155-166.

Nieto, et al., "Cloning and Development Expression of *Sna*, a Murine Homologue of the *Drosophila snail* Gene" *Development* (1992) 116: 227-237.

Niimi, et al., "SOX7 and SOX17 Regulate the Parietal Endoderm-Specific Enhancer Activity of Mouse Laminin α1 Gene" *J. Biol. Chem.* (2004) 279 (36): 38055-38061.

Niswander, L. & Martin, G.R., "*Fgf-4* Expression During Gastrulation, Myogenesis, Limb and Tooth Development in the Mouse" *Development* (1992) 114: 755-768.

Niwa, H., "Molecular mechanism to maintain stem cell renewal of ES cells" *Cell Struct Funct* (2001) 26: 137-148.

Offield, et al., "PDX-1 is Required for Pancreatic Outgrowth and Differentiation of the Rostral Duodenum" *Development* (1996) 122: 983-995.

Ogura, et al., "Behavioral abnormalities of Zic1 and Zic2 mutant mice: implications as models for human neurological disorders" *Behav Genet* (2001) 31: 317-324.

O'Hare, et al., "Conditional Immortilization of Freshly Isolated Human Mammary Fibroblast and Endothelial Cells" *Proc. Nat. Acad. Sci.* (2001) 98: 646-651.

Ormestad, et al., "Differences in the Embryonic Expression Patterns of Mouse *Foxf1* and *-2* Match Their Distinct Mutant Phenotypes" *Developmental Dynamics* (2004) 229: 328-333.

Pearce, J.J. & Evans, M.J., "*Mml*, a Mouse *Mix*-like Gene Expressed in the Primitive Streak" *Mech Dev* (1999) 87: 189-192.

Pera, et al., "Regulation of Human Embryonic Stem Cell Differentiation by BMP-2 and its Antagonist Noggin" *J Cell Sci* (2004) 117: 1269-1280.

Perea-Gomez, et al., "Initiation of Gastrulation in the Mouse Embryo is Preceded by an Apparent Shift in the Orientation of the Anterior-Posterior Axis" *Curr Biol* (2004) 14: 197-207.

Pesce, M. & Scholer, H.R., "*Oct-4*: Gatekeeper in the Beginnings of Mammalian Development" *Stem Cells* (2001) 19: 271-278.

Pevny, et al., "A Role for SOX1 in Neural Determination" *Development* (1998) 125: 1967-1978.

Phillips, et al., "Differentiation of Embryonic Stem Cells for Pharmacological Studies on Adipose Cells" *Pharmacological Research* (2003) 47:263-268.

Rajagopal, et al. "Insulin Staining of ES Cell Progeny from Insulin Uptake" *Science* (2003) 299: 363.

Rambhatla et al. "Generation of Hepatocyte-Like Cells From Human Embryonic Stem Cells." Cell Transplantation (2003), vol. 12, No. 1, p. 1-11.

Reubinoff, et al., "Embryonic Stem Cell Lines From Human Blastocysts: Somatic Differentiation In Vitro" *Nat Biotechnol* (2000) 18: 399-404.

Robb, L. & Tam, P.P., "Gastrula Organiser and Embryonic Patterning in the Mouse" *Seminars in Cell & Dev. Biol.* (2004) 15: 543-554.

Roche, et al. "Ectodermal commitment of insulin-producing cells derived from mouse embryonic stem cells" *Faseb J* (2005) 19: 1341-1343.

Rodaway, A., and Patient, R., "Mesendoderm: An Ancient Germ Layer?" *Cell* (2001) 105: 169-172.

Rodaway, et al., "Induction of the Mesendoderm in the Zebrafish Germ Ring by Yolk Cell-Derived Tgf-Beta Family Signals and Discrimination of Mesoderm and Endoderm by FGF" *Development* (1999) 126: 3067-3078.

Rohr, et al., "Zebrafish Zic1 Expression in Brain and Somites is Affected by BMP and Hedgehog Signalling" *Mech Dev* (1999) 85: 147-159.

Rossant, J. & Tam, P.P., "Emerging Asymmetry and Embryonic Patterning in Early Mouse Development" *Dev Cell* (2004) 7: 155-164.

Sander, M. and M.S. German, "The Beta Cell Transcription Factors and Development of the Pancreas" *J. Molecular Medicine* (1997) 75(5): 327-340.

Sasaki, H. & Hogan, B.L., "Differential Expression of Multiple Fork Head Related Genes During Gastrulation and Axial Pattern Formation in the Mouse Embryo" *Development* (1993) 118: 47-59.

Schier, A. F., "Nodal Signaling in Vertebrate Development" *Annu Rev Cell Dev Biol* (2003) 19: 589-621.

Schmolke, et al., "Identification of Hepatitis G Virus Particles in Human Serum by E2-Specific Monoclonal Antibodies Generated by DNA Immunization" *J. Virol.* (1998) 72: 4541-4545.

Schoenwolf, G. C., and Smith, J. L., "Gastrulation and Early Mesodermal Patterning in Vertebrates" *Methods Mol Biol* (2000) 135: 113-125.

Schuldiner, et al., "Effects of Eight Growth Factors on the Differentiation of Cell Derived from Human Embryonic Stem Cells" *Proc. Natl. Sci.* (2000) 97: 11307-11312.

Schwartz, et al. "Defined Conditions for Development of Functional Hepatic Cells from Human Embryonic Stem Cells" *Stem Cells and Development* (2005) 14(6): 643-655.

Segev, Hanna et al. "Differentiation of human embryonic stem cells into insulin-producing clusters." Stem Cells (Dayton, Ohio) 2004, vol. 22, No. 3, 2004, pp. 265-274.

Shalaby, et al., "Failure of Blood-Island Formation and Vasculogenesis in Flk-1-deficient Mice" *Nature* (1995) 376: 62-66.

Shamblott, et al., "Derivation of Pluripotent Stem Cells From Cultured Human Primordial Germ Cells" *Proc Natl Acad Sci USA* (1998) 95: 13726-13731.

Shapiro, et al., "Islet Transplantation in Seven Patients With Type 1 Diabetes Mellitus Using a Glucocorticoid-Free Immunosuppressive Regimen" *N Engl J Med* (2000) 343: 230-238.

Shapiro, et al., "Pancreatic Islet Transplantation in the Treatment of Diabetes Mellitus" *Best Pract Res Clin Endocrinol Metab* (2000) 15: 241-264.

Shapiro, et al., "Could Fewer Islet Cells be Transplanted in Type 1 Diabetes?: Insulin Independence Should be Dominant Force in Islet Transplantation" *BMJ* (2001) 322: 861.

Shi, et al., "Inducing Embryonic Stem Cells to Differentiate into Pancreatic β Cells by a Novel Three-Step Approach with Activin A and All-Trans Retinoic Acid" *Stem Cells* (2005) 23(5): 656-662.

Shiozawa, et al., "Cloning and Characterization of *Xenopus laevis* xSox7 cDNA" *Biochim Biophys Acta* (1996) 1309: 73-76.

Shirahashi, et al., "Differentiation of Human and Mouse Embryonic Stem Cells Along a Hepatocyte Lineage" *Cell Transplantation* (2004) 13: 197-211.

Shiraki, N., "TFG-β Signaling Potentiates Differentiation of Embryonic Stem Cells to Pdx-1 Expressing Endodermal Cells" *Genes to Cells* (2005) 10: 503-516.

Shook, D. & Keller, R., "Mechanisms, Mechanics and Function of Epithelial-Mesenchymal Transitions in Early Development" *Mech Dev* (2003) 120: 1351-1383.

Sinner, et al., "Sox17 and β-Catenin Cooperate to Regulate the Transcription of Endodermal Genes" *Development* (2004) 131: 3069-3080.

Skoudy, et al. "Transforming Growth Factor (TGF) beta, Fibroblast Growth Factor (FGF) and Retinoid Signaling Pathways Promote Pancreatic Exocrine Gene Expression in Mouse Embryonic Stem Cells" *Biochemical J.* (2004) 379(Pt 3): 749-756.

Smith, J., "Brachyury and the T-box Genes" *Curr Opin Genet Dev* (1997) 7: 474-480.

Smith, et al., "Upstream and Downstream From Brachyury, A Gene Required for Vertebrate Mesoderm Formation" *Cold Spring Harb Symp Quant Biol* (1997) 62: 337-346.

Soon-Shiong, P., "Treatment of Type I Diabetes using Encapsulated Islets" *Advanced Drug Delivery Reviews* (1999) 35: 259-270.

Soria, et al., "Insulin-Secreting Cells Derived from Embryonic Stem Cells Normalize Glycemia in Streptozotocin-Induced Diabetic Mice" *Diabetes* (2000) 49(2): 157-162.

Stafford, D. and Prince, V., "The Role of Retinoid Signaling in Pancreas Differentiation" *Pancreatic Development, Proliferation and Stem Cells*, Meeting Abstract, Oct. 18-19, 2001, National Institute of Health.

Stafford, D. and Prince, V., "Retinoic Acid Signaling Is Required for a Critical Early Step in Zebrafish Pancreatic Development" *Current Biology* (2002) 12: 1215-1220.

Stafford, et al., "A Conserved Role for Retoid Signaling in Vertebrate Pancreas Development" *Dev Genes Evol.* (2004) 214: 432-441.

Stainier, D.Y.R., "A Glimpse into the Molecular Entrails of Endoderm Formation" *Genes Dev* (2002) 16: 893-907.

Stemmler, et al., "Analysis of Regulatory Elements of E-Cadherin with Reporter Gene Constructs in Transgenic Mouse Embryos" *Developmental Dynamics* (2003) 227; 238-245.

Stoffers, et al., "Pancreatic Agenesis Attributable to a Single Nucleotide Deletion in the Human *IPF1* Gene Coding Sequence" *Nature Genetics* (1997) 15: 106-110.

Stoffers, et al., "Early-onset Type-II Diabetes Mellitus (MODY4) Linked to *IPF1*" *Nature Genetics* (1997) 17: 138-139.

Sun, et al., "Targeted Disruption of *Fgf8* Causes Failure of Cell Migration in the Gastrulating Mouse Embryo" *Genes Dev* (1999) 13: 1834-1846.

Suzuki, et al., "Cloned Cells Develop Renal Cortical Collecting Tubles" *Nephron.* (1994) 68: 118-124.

Tada, et al. "Characterization of Mesendoderm: A Diverging Point of the Definitive Endoderm and Mesoderm in Embryonic Stem Cell Differentiation Culture" *Development* (2005) 132: 4363-4374.

Takash, et al., "SOX7 Transcription Factor: Sequence, Chromosomal Localisation, Expression, Transactivation and Interference With Wnt Signalling" *Nucleic Acids Res* (2001) 29: 4274-4283.

Takahashi, et al., "Induction of Pluripotent Stem Cells from Adult Human Fibroblasts by Defined Factors" *Cell* (2007) 131: 861-872.

Tam et al., "Early Endoderm Development in Vertebrates: Lineage Differentation and Morphogenetic Function" *Curr Opin Genet Dev.* (2003) 13(4): 393-400.

Tam, et al., "Gene Function in Mouse Embryogenesis: Get Set for Gastrulation" *Nat. Rev. Genet.* (2007) 8(5): 368-381.

Taniguchi, et al., "Isolation and Characterization of a Mouse SRY-related cDNA, mSox7" *Biochim Biophys Acta* (1999) 1445: 225-231.

Technau, U. "Brachyury, the Blastopore and the Evolution of the Mesoderm" *Bioessays* (2001) 23: 788-794.

Thomas, et al., "The Murine Gene, *Traube*, Is Essential for the Growth of Preimplantation Embryos" *Dev Biol* (2000) 227: 324-342.

Thomson, et al., "Embryonic Stem Cell Lines Derived from Human Blastocysts" *Science* (1998) 282: 1145-1147.

Tiedemann, et al., "Pluripotent cells (stem cells) and Their Determination and Differentiation in Early Vertebrate Embryogenesis" *Develop. Growth Differ.* (2001) 43: 469-502.

Tremblay, et al., "Formation of the definitive endoderm in mouse is a Smad2-dependent process" *Development* (2000) 127: 3079-3090.

Trueba, et al., "*PAX8, TITF1*, and *FOXE1* Gene Expression Patterns during Human Development: New Insights into Human Thyroid Development and Thyroid Dysgenesis-Associated Malformations" *J. Clinical Endocrinology & Metabolism* (2005) 90(1): 455-462.

Ulivieri, et al., "Generation of a Monoclonal Antibody to a Defined Portion of the Heliobacter Pylori Vacuolating Cytotoxin by DNA Immunization" *J. Biotechnol.* (1996) 51: 191-194.

Urbach, et al., "Modeling Lesch-Nyhan Disease by Gene Targeting in Human Embryonic Stem Cells" *Stem Cells* (2004) 22: 635-641.

Valdimarsdottir, et al., "Function of the TGFβ Superfamily in Human Embryonic Stem Cells" *APMIS* (2005) 113: 773-789.

Vallier, et al. "Activin/Nodal and FGF Pathways Cooperate to Maintain Pluripotency of Human Embryonic Stem Cells" *J Cell Sci.* (2005) 118: 4495-509.

Vallier et al. "Nodal Inhibits Differentiation of Human Embryonic Stem Cells Along the Neuroectodermal Default Pathway" (2004) *Developmental Biology* 275, 403-421.

Vandesompele, et al., "Accurate Normalization of Real-Time Quantitative RT-PCR Data by Geometric Averaging of Multiple Internal Control Genes" *Genome Biol* (2002) 3(7): 1-12.

Varlet, et al., "Nodal Expression in the Primitive Endoderm is Required for Specification of the Anterior Axis During Mouse Gastrulation" *Development* (1997) 124: 1033-1044.

Vincent, et al., "Cell Fate Decisions Within the Mouse Organizer Are Governed by Graded Nodal Signals" *Genes Dev* (2003) 17: 1646-1662.

Vogel, G. "Stem Cells are Coaxed to Produce Insulin" *Science* (2001) 292: 615-616.

Wang, et al. "Self-Renewal of Human embryonic Stem Cells Requires Insulin-Like Growth Factor-1 Receptor and ERBB2 Receptor Signaling." Blood (2007), 110; 4110-4119.

Wei, et al., "Transcriptome Profiling of Human and Murine ESCs Identifies Divergent Paths Required to Maintain the Stem Cell State" *Stem Cells* (2005) 23: 166-185.

Weiler-Guettler, et al., "Developmentally Regulated Gene Expression of Thrombomodulin in Postimplantation Mouse Embryos" *Development* (1996) 122: 2271-2281.

Weiler-Guettler, et al., "Thrombomodulin Gene Regulation by cAMP and Retinoic Acid in F9 Embryonal Carcinoma Cells" *PNAS* (1992) 89: 2155-2159.

Weinstein, D.C. et al. The winged-helix transcription factor HNF-3 beta is required for notochord development in the mouse embryo. Cell 78, 575-588 (1994).

Wells, J. M., and Melton, D. A., "Vertebrate Endoderm Development" *Annu Rev Cell Dev Biol* (1999) 15: 393-410.

Wells, J. M., and Melton, D. A. "Early Mouse Endoderm is Patterned by Soluble Factors From Adjacent Germ Layers" *Development* (2000) 127: 1563-1572.

Wilding et al., "The Role of *pdx1* and *HNF6* in Proliferation and Differentiation of Endocrine Precedures" *Diabetes Metab Res Rev.* (2004) 20(2): 114-23.

Willison, K., "The Mouse Brachyury Gene and Mesoderm Formation" *Trends Genet* (1990) 6: 104-105.

Xu, et al., "Characterization and Enrichment of Cardiomyocytes Derived From Human Embryonic Stem Cells" *Cellular Biology* (2002) 91: 501-508.

Xu, et al., "Feeder-Free Growth of Undifferentiated Human Embryonic Stem Cells" *Nature Biotechnology* (2001) 19: 971-974.

Xu, et al., "BMP4 Initiates Human Embryonic Stem Cell Differentiation to Trophoblast" *Nat Biotechnol* (2002) 20: 1261-1264.

Yamaguchi, et al., "*flk-1*, an *flt*-related Receptor Tyrosine Kinase is an Early Marker for Endothelial Cell Precursors" *Development* (1993) 118: 489-498.

Yamaguchi, et al., "*T* (Brachyury) is a Direct Target of Wnt3a During Paraxial Mesoderm Specification" *Genes Dev* (1999) 13: 3185-3190.

Yang, et al., "Disabled-2 is Essential for Endodermal Cell Positioning and Structure Formation During Mouse Embryogenesis" *Dev Biol* (2002) 251: 27-44.

Yasunaga, et al. "Induction and Monitoring of Definitive and Visceral Endoderm Differentiation of Mouse ES Cells" *Nature Biotechnology* (2005) 23: 1542-1550.

Ying, et al., "BMP Induction of Id Proteins Suppresses Differentiation and Sustains Embryonic Stem Cell Self-Renewal in Collaboration with STAT3" *Cell* (2003) 115: 281-292.

Yusuf et al., "Expression of Chemokine Receptor CXCR4 During Chick Embryo Development" *Anat Embryol* (2005) 210(1): 35-41.

Zhao, G. Q., "Consequences of Knocking Out BMP Signaling in the Mouse" *Genesis* (2003) 35: 43-56.

Zhou, et al., "Nodal is a Novel TGF-beta-like Gene Expressed in the Mouse Node during Gastrulation" *Nature* (1993) 361: 543-547.

Zwaka, et al. "Homologous Recombination in Human Embryonic Stem Cells" *Nature Biotechnology* (2003) 21: 319-321.

International Search Report dated Jun. 5, 2008, issued in International Application No. PCT/US07/080589.

* cited by examiner

```
  1 MGPWSRSLSA LLLLLQVSSW LCQEPEPCHP GFDAESYTFT VPRRHLERGR VLGRVNFEDC
 61 TGRQRTAYFS LDTRFKVGTD GVITVKRPLR FHNPQIHFLV YAWDSTYRKF STKVTLNTVG
121 HHHRPPPHQA SVSGIQAELL TFPNSSPGLR RQKRDWVIPP ISCPENEKGP FPKNLVQIKS
181 NKDKEGKVFY SITGQGADTP PVGVFIIERE TGWLKVTEPL DRERIATYTL FSHAVSSNGN
241 AVEDPMEILI TVTDQNDNKP EFTQEVFKGS VMEGALPGTS VMEVTATDAD DDVNTYNAAI
301 AYTILSQDPE LPDKNMFTIN RNTGVISVVT TGLDRESFPT YTLVVQAADL QGEGLSTTAT
361 AVITVTDTND NPPIFNPTTY KGQVPENEAN VVITTLKVTD ADAPNTPAWE AVYTILNDDG
421 GQFVVTTNPV NNDGILKTAK GLDFEAKQQY ILHVAVTNVV PFEVSLTTST ATVTVDVLDV
481 NEAPIFVPPE KRVEVSEDFG VGQEITSYTA QEPDTFMEQK ITYRIWRDTA NWLEINPDTG
541 AISTRAELDR EDFEHVKNST YTALIIATDN GSPVATGTGT LLLILSDVND NAPIPEPRTI
601 FFCERNPKPQ VINIIDADLP PNTSPFTAEL THGASANWTI QYNDPTQESI ILKPKMALEV
661 GDYKINLKLM DNQNKDQVTT LEVSVCDCEG AAGVCRKAQP VEAGLQIPAI LGILGGILAL
721 LILILLLLLF LRRRAVVKEP LLPPEDDTRD NVYYYDEEGG GEEDQDFDLS QLHRGLDARP
781 EVTRNDVAPT LMSVPRYLPR PANPDEIGNF IDENLKAADT DPTAPPYDSL LVFDYEGSGS
841 EAASLSSLNS SESDKDQDYD YLNEWGNRFK KLADMYGGGE DD (SEQ ID NO:1)
```

*Figure 1*

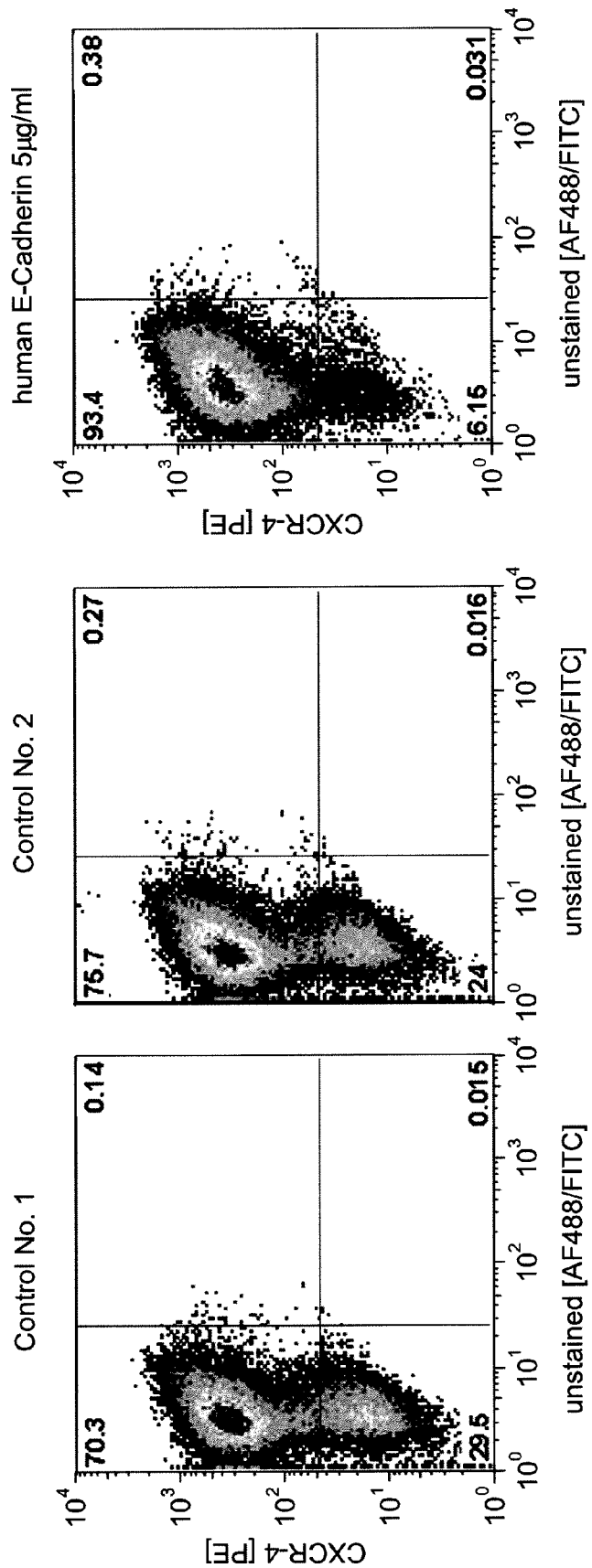

METHODS FOR INCREASING DEFINITIVE ENDODERM PRODUCTION

SEQUENCE LISTING

The present application is being filed along with a Sequence Listing in electronic format. The Sequence Listing is provided as a file entitled CYTHERA-60A-SEQ.TXT, created Sep. 24, 2007, which is 9 Kb in size. The information in the electronic format of the Sequence Listing is incorporated herein by reference in its entirety.

FIELD OF THE INVENTION

The present invention relates to the fields of medicine and cell biology. In particular, the present invention relates to methods comprising efficient production of definitive endoderm and compositions thereof.

BACKGROUND

Human pluripotent stem cells, such as embryonic stem (ES) cells and embryonic germ (EG) cells, were first isolated in culture without fibroblast feeders in 1994 (Bongso et al., 1994) and with fibroblast feeders (Hogan, 1997). Later, Thomson, Reubinoff and Shamblott established continuous cultures of human ES and EG cells using mitotically inactivated mouse feeder layers (Reubinoff et al., 2000; Shamblott et al., 1998; Thomson et al., 1998).

Two properties that make human embryonic stem cells (hESCs) uniquely suited to cell therapy applications are pluripotence and the ability to maintain these cells in culture for prolonged periods. Pluripotency is defined by the ability of hESCs to differentiate to derivatives of all three (3) primary germ layers (endoderm, mesoderm, ectoderm) which, in turn, form all somatic cell types of the mature organism in addition to extraembryonic tissues (e.g. placenta) and germ cells. Owing to the large variety of cell types that may arise in differentiating hESC cultures, the vast majority of cell types are produced at very low efficiencies. Hence, improving the efficiency of directed differentiation of hESCs, or conversion of the hESCs to various differentiated derivatives, is advantageous.

SUMMARY OF THE INVENTION

In one embodiment of the invention, there is provided an in vitro method for increasing the definitive endoderm production by contacting an agent with a human embryonic stem cell (hESC) culture in a first medium, wherein the culture comprises at least one E-cadherin expressing cell, and wherein the agent selectively binds to E-cadherin on the E-cadherin expressing cell and inhibits adhesion of the E-cadherin expressing cell to another cell; and differentiating the hESC culture in a second medium comprising a growth factor of the Nodal/Activin subgroup of the TGFβ superfamily, thereby increasing definitive endoderm (DE) production.

In another embodiment of the invention, there is provided a method for identifying an agent capable of increasing production of a cell derived from a human embryonic stem cell (hESC) by contacting a hESC in the presence of an agent in a culture medium, wherein the agent binds to extracellular calcium ions in the medium; differentiating the hESC culture in the culture; measuring production of the differentiated cell in the presence of the agent, wherein production of the differentiated cell in the presence of the agent is increased as compared to production of the differentiated cell in the absence of the agent, thereby indicating an agent capable of increasing production of a human embryonic derived cell.

Still, in another embodiment of the invention, there is provided an in vitro composition containing an antagonist specifically binding to an E-cadherin expressing cell, wherein the cell comprises a human embryonic stem cell (hESC), and wherein binding of the antagonist to the cell inhibits cellular adhesion of the E-cadherin expressing cell.

In another embodiment of the invention, there is provided a cell culture containing calcium binding agent and an E-cadherin expressing cell in a culture medium, wherein the cell comprises a human embryonic stem cell (hESC), and wherein the agent binds to extracellular calcium ions in the culture medium.

In still another embodiment of the invention, there is provided a method of identifying an E-cadherin agonist or antagonist by providing a peptide library based on hESCs and an E-cadherin peptide; screening said peptide library for agents having high affinity binding to the E-cadherin peptide; and selecting a member of the peptide library binding to the E-cadherin peptide wherein the affinity of the member is equivalent or higher than that of a native homotypic E-cadherin peptide.

Other aspects of the present invention are set forth in the numbered paragraphs below:

1. An in vitro method for increasing definitive endoderm production comprising providing an agent to a cell culture comprising E-cadherin-expressing human embryonic stem cells, thereby inhibiting adhesion of the E-cadherin-expressing cells to each other; and differentiating said E-cadherin-expressing human embryonic stem cells by contacting said cells with a medium comprising a growth factor of the Nodal/Activin subgroup of the TGFβ superfamily of growth factors, thereby increasing the production of definitive endoderm.

2. The method of paragraph 1, wherein the agent binds E-cadherin.

3. The method of paragraph 2, wherein the agent is an antagonist of E-cadherin.

4. The method of paragraph 3, wherein the antagonist is a polyclonal or a monoclonal E-cadherin antibody, wherein the agent is a peptide or peptide analog.

5. The method of paragraph 1 wherein the agent is a peptide or a peptide analog.

6. The method of paragraph 5, wherein the peptide is an E-cadherin peptide corresponding to an E-cadherin extracellular domain at amino acid residues 600-700 of human E-cadherin (SEQ ID NO:1).

7. The method of paragraph 1, wherein the agent is a calcium ion chelator.

8. The method of paragraph 7, wherein the calcium ion chelator is selected from the group consisting of ethylenediaminetetraacetic acid (EDTA), ethyleneglycoltetraacetic acid (EGTA), 1,10 phenanthroline, diethylenetriaminepentaacetate (DTPA), hydroxyethylethylenediaminetriacetic acid (HEEDTA), diaminocyclohexanetetraacetic acid (CDTA), 1,2-Bis(2-aminophenoxy)ethane-N,N,N',N'-tetraacetic acid (BAPTA), and pharmaceutically acceptable salts thereof.

9. The method of paragraph 1, wherein said E-cadherin-expressing human embryonic stem cells are provided with said agent in a first medium, and wherein said E-cadherin-expressing human embryonic stem cells are differentiated in a second medium.

10. The method of paragraph 1, wherein said first medium is different from said second medium.

11. A method for identifying an agent capable of increasing production of a cell derived from a human embryonic stem cell, said method comprising providing a candidate agent to a human embryonic stem cell culture; differentiating the human embryonic stem cell in a culture medium comprising a differentiation factor known to be capable of promoting the differentiation of said human embryonic stem cells; and determining whether the candidate agent increases the production of cells differentiated from said human embryonic stem cells by comparing the production of differentiated cells in said cell culture provided with the candidate agent to the production of differentiated cells in a human embryonic stem cell culture that has not been provided with said candidate agent but has been treated with the same differentiation factor as the cell culture provided with the candidate agent, wherein greater production of differentiated cells in the cell culture provided with the candidate agent as compared to the production of differentiated cells in the cell culture not provided with the candidate agent indicates that the candidate agent increases the production of a cell derived from a human embryonic cell.

12. The method of paragraph 11, wherein the differentiation factor is a growth factor of the Nodal/Activin subgroup of the TGFβ superfamily.

13. The method of paragraph 11, wherein the differentiated cell is a definitive endoderm cell or derivative thereof.

14. The method of paragraph 11, wherein the agent is an antagonist of human E-cadherin.

15. The method of paragraph 11, wherein the agent is a synthetic compound.

16. The method of paragraph 15, wherein the agent is a natural product.

17. An in vitro composition comprising an antagonist of E-cadherin specifically bound to an E-cadherin-expressing human embryonic stem cells, wherein the binding of the antagonist inhibits adhesion between said embryonic stem cells.

18. The composition of paragraph 17, wherein the antagonist is a polyclonal or a monoclonal E-cadherin antibody.

19. The composition of paragraph 17, wherein at least 10% of the human embryonic stem cells are not adhered to other human embryonic stem cells.

20. The composition of paragraph 17, wherein at least 50% of the human embryonic stem cells are not adhered to other human embryonic stem cells.

21. A cell culture comprising a calcium-binding agent and E-cadherin-expressing human embryonic stem cells in a culture medium, wherein the calcium-binding agent is bound to calcium ions in the culture medium, thereby inhibiting adhesion between said embryonic stem cells.

22. The cell culture of paragraph 19, wherein the calcium binding agent is selected from the group consisting of ethylenediaminetetraacetic acid (EDTA), ethyleneglycoltetraacetic acid (EGTA), 1,10 phenanthroline, diethylenetriaminepentaacetate (DTPA), hydroxyethylethylenediaminetriacetic acid (HEEDTA), diaminocyclohexanetetraacetic acid (CDTA), 1,2-Bis(2-aminophenoxy)ethane-N,N,N',N'-tetraacetic acid (BAPTA), and pharmaceutically acceptable salts thereof.

23. The composition of paragraph 21, wherein at least 10% of the human embryonic stem cells are not adhered to other human embryonic stem cells.

24. The composition of paragraph 21, wherein at least 50% of the human embryonic stem cells are not adhered to other human embryonic stem cells.

25. A method of identifying an E-cadherin agonist or antagonist comprising providing a peptide library of peptides derived from hESCs and an E-cadherin peptide; screening said peptide library for peptides having high affinity binding to the E-cadherin peptide; and selecting a member of the peptide library binding to the E-cadherin peptide wherein the affinity of the member is equivalent to or higher than that of a native homotypic E-cadherin peptide.

26. An in vitro method for increasing definitive endoderm (DE) production comprising contacting an agent with a human embryonic stem cell (hESC) culture in a first medium, wherein the culture comprises at least one E-cadherin expressing cell, and wherein the agent selectively binds to E-cadherin on the E-cadherin expressing cell and inhibits contact of the E-cadherin expressing cell to another cell; and differentiating the hESC culture in a second medium comprising a growth factor of the Nodal/Activin subgroup of the TGFβ superfamily, thereby increasing DE production.

27. The method of paragraph 26, wherein the agent is an agonist or an antagonist.

28. The method of paragraph 26, wherein the agent is a peptide or peptide analog.

29. The method of paragraph 27, wherein the antagonist is a polyclonal or a monoclonal E-cadherin antibody.

30. The method of paragraph 28, wherein the peptide is an E-cadherin peptide corresponding to an E-cadherin extracellular domain at amino acid residues 600-700 of human E-cadherin (SEQ ID NO:1).

31. A method for identifying an agent capable of increasing production of a cell derived from a human embryonic stem cell (hESC) comprising contacting a hESC in the presence of an agent in a culture medium, wherein the agent binds to extracellular calcium ions in the medium; differentiating the hES cells in the culture medium; and measuring production of the differentiated cell in the presence of the agent, wherein production of the differentiated cell in the presence of the agent is increased as compared to production of the differentiated cell in the absence of the agent, thereby indicating an agent capable of increasing production of a differentiated cell derived from a human embryonic cell.

32. The method of paragraph 31, wherein the culture medium further comprises a growth factor of the Nodal/Activin subgroup of the TGFβ superfamily.

33. The method of paragraph 31, wherein the differentiated cell is a definitive endoderm cell or derivative thereof.

34. The method of paragraph 31, wherein the agent is a calcium ion chelator.

35. The method of paragraph 34, wherein the calcium ion chelator is selected from the group consisting of ethylenediaminetetraacetic acid (EDTA), Ethyleneglycoltetraacetic acid (EGTA), Diethylenetriaminepentaacetate (DTPA), Hydroxyethylethylenediaminetriacetic acid (HEEDTA), Diaminocyclohexanetetraacetic acid (CDTA), 1,2-Bis(2-aminophenoxy)ethane-N,N,N',N'-tetraacetic acid (BAPTA), and pharmaceutically acceptable salts thereof.

36. An in vitro composition comprising an antagonist specifically binding to an E-cadherin expressing cell, wherein the cell comprises a human embryonic stem cell (hESC), and wherein binding of the antagonist to the cell inhibits cellular adhesion of the E-cadherin expressing cell.

37. The composition of paragraph 36, wherein the antagonist is a polyclonal or a monoclonal E-cadherin antibody.

38. A cell culture comprising a calcium binding agent and an E-cadherin expressing cell in a culture medium, wherein the cell comprises a human embryonic stem cell (hESC), and wherein the agent binds to extracellular calcium ions in the culture medium.

39. The cell culture of paragraph 38, wherein the calcium binding agent is selected from the group consisting of ethylenediaminetetraacetic acid (EDTA), Ethyleneglycoltetraacetic acid (EGTA), Diethylenetriaminepentaacetate (DTPA), Hydroxyethylethylenediaminetriacetic acid (HEEDTA), Diaminocyclohexanetetraacetic acid (CDTA), 1,2-Bis(2-aminophenoxy)ethane-N,N,N',N'-tetraacetic acid (BAPTA), and pharmaceutically acceptable salts thereof.

40. A method of identifying an E-cadherin agonist or antagonist comprising providing a peptide library based on hESCs and an E-cadherin peptide; screening said peptide library for agents having high affinity binding to the E-cadherin peptide; selecting a member of the peptide library binding to the E-cadherin peptide wherein the affinity of the member is equivalent or higher than that of a native homotypic E-cadherin peptide.

Additional embodiments of the present invention may also be found in U.S. Provisional Patent Application No. 60/532,004, entitled DEFINITIVE ENDODERM, filed Dec. 23, 2003; U.S. Provisional Patent Application No. 60/566,293, entitled PDX1 EXPRESSING ENDODERM, filed Apr. 27, 2004; U.S. Provisional Patent Application No. 60/586,566, entitled CHEMOKINE CELL SURFACE RECEPTOR FOR THE ISOLATION OF DEFINITIVE ENDODERM, filed Jul. 9, 2004; U.S. Provisional Patent Application No. 60/587,942, entitled CHEMOKINE CELL SURFACE RECEPTOR FOR THE ISOLATION OF DEFINITIVE ENDODERM, filed Jul. 14, 2004; U.S. patent application Ser. No. 11/021,618, entitled DEFINITIVE ENDODERM, filed Dec. 23, 2004; U.S. patent application Ser. No. 11/165,305, entitled METHODS FOR IDENTIFYING FACTORS FOR DIFFERENTIATING DEFINITIVE ENDODERM, filed Jun. 23, 2005; and U.S. Provisional Patent Application No. 60/736,598, entitled MARKERS OF DEFINITIVE ENDODERM, filed Nov. 14, 2005.

These and other aspects of the invention, as well as various advantages and utilities, will be more apparent with reference to the detailed description of the preferred embodiments.

BRIEF DESCRIPTION OF THE DRAWINGS

FIG. 1 is the deduced amino acid sequence of human E-cadherin. Signature E-cadherin motifs are bolded and underlined. The first amino acid of the mature protein is underlined twice.

FIGS. 2A-C are flow cytometry dot plots of hESC-derived cells that have been treated to differentiate to definitive endoderm cells post-treatment with anti-human E-cadherin (5 μg/mL) and labeled using a fluorescently conjugated CXCR4 antibody. FIGS. 2A, B & C (top left quadrant) show the proportion of cells that are CXCR4 positive following analysis.

FIG. 3B), NANOG (FIG. 3C), and OCT4 (FIG. 3D). The abbreviations are indicated as follows: 1d and 3d—days 1 and 3, respectively; no AB—no anti-human E-cadherin antibody.

FIG. 4B) and Cerberus (CER; FIG. 4C). The abbreviations are indicated as follows: ESC—embryonic stem cell; PBS$^{-/-}$—PBS with no calcium and no magnesium; PBS$^{+/+}$—PBS with calcium and magnesium; A100—100 ng/ml activin A; and W25—25 ng/ml Wnt3a.

DETAILED DESCRIPTION OF THE INVENTION

Figure 3A:
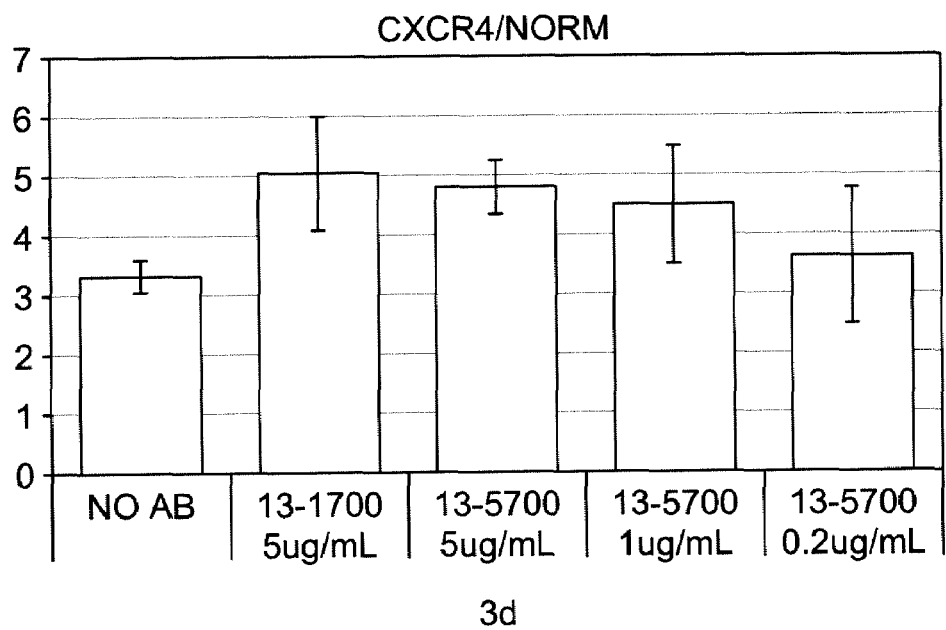
FIGS. 3A-D are bar charts showing the mRNA levels of certain markers as detected by QPCR in hESC derived cells that have been treated to differentiate to definitive endoderm cells along with treatment with anti-human E-cadherin. Specifically shown are the mRNA levels of CXCR4 (FIG. 3A), Cerberus (CER.
Figure 3B:
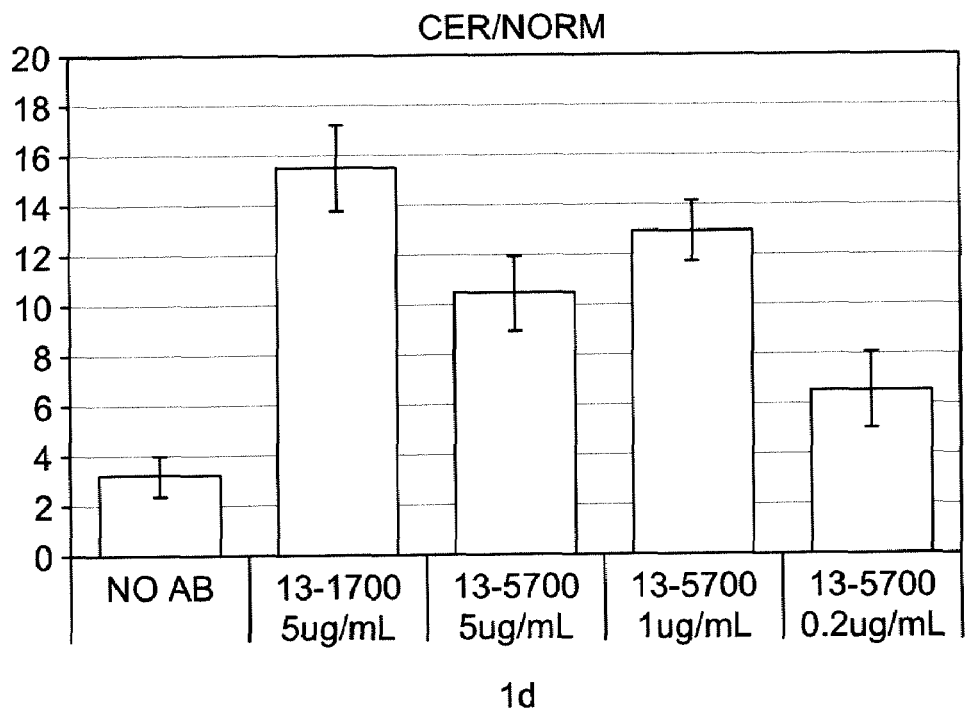

A crucial stage in early human development termed gastrulation occurs 2-3 weeks after fertilization. Gastrulation is extremely significant because it is at this time that the three primary germ layers are first specified and organized (Lu et al., Curr Opin Genet Dev 11, 384-392 (2001); Schoenwolf and Smith, Methods Mol Biol 135, 113-125 (2000). The ectoderm is responsible for the eventual formation of the outer coverings of the body and the entire nervous system whereas the heart, blood, bone, skeletal muscle and other connective tissues are derived from the mesoderm. Definitive endoderm is defined as the germ layer that is responsible for formation of the entire gut tube which includes the esophagus, stomach and small and large intestines, and the organs which derive from the gut tube such as the lungs, liver, thymus, parathyroid and thyroid glands, gall bladder and pancreas [Grapin-Botton and Melton, Trends Genet. 16, 124-130 (2000); Kimelman and Griffin, Curr Opin Genet Dev 10, 350-356 (2000); Tremblay et al., Development 127, 3079-3090 (2000); Wells and Melton, Annu Rev Cell Dev Biol 15, 393-410 (1999); Wells and Melton, Development 127, 1563-1572 (2000)]. A very important distinction should be made between the definitive endoderm and the completely separate lineage of cells termed primitive endoderm. The primitive endoderm is primarily responsible for formation of extra-embryonic tissues, mainly the parietal and visceral endoderm portions of the placental yolk sac and the extracellular matrix material of Reichert's membrane.

During gastrulation, the process of definitive endoderm formation begins with a cellular migration event in which mesendoderm cells (cells competent to form mesoderm or endoderm) migrate through a structure called the primitive streak. Definitive endoderm is derived from cells, which migrate through the anterior portion of the streak and through the node (a specialized structure at the anterior-most region of the streak). As migration occurs, definitive endoderm populates first the most anterior gut tube and culminates with the formation of the posterior end of the gut tube.

While not intending to be bound by any particular theory, it is believed that E-cadherin causes hESCs to be tightly associated thereby inhibiting efficient directed differentiation of the cells in vitro. Accordingly, certain aspects of the present invention relate to agents which bind to E-cadherin on at least one E-cadherin expressing cell, for example, an hESC. In some embodiments, the agents bind selectively and/or specifically to E-cadherin. It is believed that the binding of E-cadherin decreases cellular adhesion and/or results in cell signaling events, thereby increasing the efficiency of directed differentiation of definitive endoderm (DE) derived from the hESCs. Other aspects of the present invention relate to methods for identifying agents which selectively or specifically bind to E-cadherin and/or an E-cadherin expressing cell, and which binding increases the efficiency of directed differentiation of DE from hESCs.

Although the following description is directed to a preferred embodiment of the present invention, namely, compositions and methods for increasing the efficiency of DE production from hESCs, it should be understood that this description is illustrative only and is not intended to limit the scope of the present invention. Thus, in its broadest sense, the present invention relates to the discovery that agents (e.g., antagonists), which disrupt epithelial interactions and facilitate differentiation. For example, antagonists that selectively and specifically bind to E-cadherin, modulate cellular adhesion by inhibiting E-cadherin homophilic or heterophilic cellto-cell contacts, and increase differentiation efficiency (e.g., increase differentiation efficiency of definitive endoderm).

The adhesive interactions of cells with other cells (homotypic and heterotypic) and between cells and the extracellular matrix play critical roles in a wide variety of processes including, for example, regulation of developmental processes, modulation of the immune system, and tumor progression and metastasis. Cellular adhesion is the binding of a cell to another cell (homotypic and heterotypic) or to a surface or matrix. Cellular adhesion is regulated by specific adhesion molecules, which transduce information from the extracellular to the intracellular matrix. e.g., cadherins that interact with molecules on the opposing cell or surface. Such adhesion molecules are also termed "receptors" and the molecules they recognize are termed "ligands" (and sometimes "counter-receptors"). Therefore, the study of cell adhesion involves cell adhesion proteins and the molecules that they bind to.

At least three families of adhesion molecules mediate these interactions: the integrins, the cadherins and the selectins. In general, adhesion molecules are transmembrane proteins which contain an extracellular domain for interacting with an extracellular matrix or cellular component, a transmembrane domain spanning the cell membrane and a cytoplasmic domain for interacting with one or more cytoskeletal components.

The integrins represent one of the best characterized families of adhesion receptors. Integrins are glycoprotein heterodimers which contain a noncovalently-associated α and β subunit. There are at least fourteen known α subunits and eight known β subunits which can pair to form at least twenty different integrin molecules. Still, several distinct integrin α chains are capable of pairing with one type of β chain to form a β chain subfamily.

Selectins are a family of transmembrane molecules, expressed on the surface of leukocytes and activated endothelial cells. Selectins contain an N-terminal extracellular domain with structural homology to calcium-dependent lectins, followed by a domain homologous to epidermal growth factor, and two to nine consensus repeats (CR) similar to sequences found in complement regulatory proteins. Each of these adhesion receptors is inserted via a hydrophobic transmembrane domain and possesses a short cytoplasmic tail.

The cadherins constitute a superfamily that share a basic structure. They play an important role in the establishment and maintenance of intercellular connections between cells of the same type (homotypic; reviewed in Geiger B. et al. (1992) *Annual Review of Cell Biology* 8:307; Kemler R. (1993) *Trends in Gastroenterology* 9:317; Takeichi M. (1990) *Annual Review of Biochem.* 59:237; Takeichi M. (1991) *Science* 251: 1451; Bussemakers, M. et al (1993) *Mol. Biol. Rep.* 17 (2), 123-128). The cadherins are synthesized as precursors that are cleaved during post-translational processing. The mature cadherins are single chain molecules which include relatively large extracellular domains, a single transmembrane region and a cytoplasmic tail. The members of the cadherin family share homology to each other. For example, epithelial cadherin, or E-cadherin, is a 120-kDa transmembrane glycoprotein expressed mainly on the surface of epithelial cells. Bussemakers et al. supra describe that the mature human E-cadherin amino acid sequence (FIG. 1; SEQ ID NO: 1) is about 76% homologous to human P-cadherin and about 67% to N-cadherin. Within the extracellular domains, characteristic sequences of four to five amino acids, LDRE and DXNDN, which are bolded/underlined in FIG. 1) are well conserved among all cadherins. In particular, the sequence DXNDNXP (bolded/underlined in FIG. 1), is thought to bind divalent calcium and is generally believed to be essential for cadherin function. Two additional, less well conserved domains are located proximal to the membrane. Among the classical cadherins (i.e., P-(placenta), E-(epithelial), and N-(neural) cadherin), the cytoplasmic domain contains the highest degree of homology, followed by the first extracellular, or ecto-, domain (Takeichi M. (1990) *Annual Review of Biochem.* 59:237). The cytoplasmic or intracellular domain contains a highly phosphorylated region vital to β-catenin binding and therefore to cadherin function. Beta-catenin can also bind to α-catenin, which participates in regulation of actin-containing cytoskeletal filaments. There are also various calcium binding sites throughout the amino acid sequence (Bussemakers, M. et al supra; Kemler R. (1993) *Trends in Gastroenterology* 9:317).

The best characterized function of E-cadherin are homotypic interactions, i.e. each class will only bind to members of the same class such as, N-cadherin will bind only to another N-cadherin molecule. Because of this specificity, groups of cells that express the same type of cadherin molecule tend to cluster and "stick" together during development, while cells expressing different types of cadherin binding molecules (heterotypic) tend to separate. It is generally believed that sequences in the EC-1 extracellular domain are necessary to mediate homotypic (i.e., cadherin-to-cadherin) binding. Swapping experiments in which part of the E-cadherin molecule is replaced with a corresponding portion of the P-cadherin molecule have been used to identify the amino acid portions of post-translationally processed cadherin that are required for biological activity. In particular, Nose et al. (1990) report that an HAV tripeptide sequence is essential for homotypic cadherin binding. Nose et al. (1990) *Cell* 61:147. Further, Takeichi report that the amino acid residues flanking the HAV tripeptide sequence also contribute to homotypic binding specificity. (Takeichi M. (1991) *Science* 251:1451). A review of the literature indicates that research directed to understanding cadherin-mediated adhesion has focused on efforts to elucidate the mechanism underlying cadherin-mediated homotypic cell adhesion. Although homotypic E-cadherin interactions are well-characterized, little attention has been directed to studying, if any, heterotypic E-cadherin interactions, Whittard et al. showed that E-cadherin is capable of heterotypic interactions, i.e., an E-cadherin expressing cell binding to a non-E-cadherin ligand on a different, and non-E-cadherin expressing cell type (*Matrix Biol.* 2002 21(6): 525-32). Whittard et al. demonstrated that E-cadherin interacts with integrins expressed on non-leukocytic-cells based on cell adhesion. Whittard et al. suggests that heterotypic interactions between E-cadherins and integrins, for example, may be more common than originally thought.

Accordingly, although not intending to be bound by any particular theory, it is believed that E-cadherin mediated binding of hESCs to each other inhibits their directed differentiation to other cell types. Improved and/or increased efficiency of directed differentiation of DE and other cell types derived from hESCs is facilitated, at least in part, by inhibiting the intercellular adhesion of hESCs. Accordingly, certain aspects of the present invention provide compositions and methods for increasing the efficiency of DE production from hESCs by inhibiting their cell-to-cell adhesions.

Definitions

In one embodiment of the invention, there is provided isolated agents which antagonize and/or inhibit in vitro cellular adhesion between E-cadherin expressing cells, e.g., hESCs, or matrix. In some embodiments, the agents can be homotypic and selectively and specifically bind to E-cadherin expressing cells, or they can be non-E-cadherin ligands which selectively and specifically bind to E-cadherin (heterotypic). According to one aspect of the invention, the agent is a polypeptide, functional peptide fragment or a portion of a polypeptide that has one or more sequences related to, or derived from, the amino acid sequence of the extracellular domain of E-cadherin. For example, an E-cadherin derived peptide can bind to an E-cadherin-expressing cell (homotypic) or to an E-cadherin cognate of a non-E-cadherin expressing cell (heterotypic).

When used in connection with an E-cadherin, the term "fragment" or "portion" means any non-zero amount of the full length E-cadherin polypeptide. In preferred embodiments, the term "fragment" or "portion" means at least 5%, at least 6%, at least 7%, at least 8%, at least 9%, at least 10%, at least 11%, at least 12%, at least 13%, at least 14%, at least 15%, at least 16%, at least 17%, at least 18%, at least 19%, at least 20%, at least 21%, at least 22%, at least 23%, at least 24%, at least 25%, at least 26%, at least 27%, at least 28%, at least 29%, at least 30%, at least 31%, at least 32%, at least 33%, at least 34%, at least 35%, at least 36%, at least 37%, at least 38%, at least 39%, at least 40%, at least 41%, at least 42%, at least 43%, at least 44%, at least 45%, at least 46%, at least 47%, at least 48%, at least 49%, at least 50%, at least 51%, at least 52%, at least 53%, at least 54%, at least 55%, at least 56%, at least 57%, at least 58%, at least 59%, at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 96%, at least 97%, at least 98%, and at least 99% of the full length E-cadherin polypeptide.

As used herein, reference to a polypeptide, peptide, or functional fragment thereof, embraces peptides of the extracellular E-cadherin domain(s), as well as functionally equivalent peptide analogs of the foregoing peptide fragments. For example, an isolated E-cadherin peptide is obtained by isolating the extracellular cleavage product of E-cadherin that results following exposure of epithelial cells to trypsin in the presence of divalent calcium. Trypsin cleavage yields an approximately 80 kD fragment of E-cadherin containing a portion of the extracellular domain. Thus, this particularly preferred peptide has an amino acid sequence corresponding to the naturally occurring proteolytic cleavage site of E-cadherin.

In some embodiments, the phrase "isolated peptides" refers to a cloned expression product of a nucleic acid or oligonucleotide, a peptide which is isolated following cleavage from a larger polypeptide or a peptide that is synthesized, e.g., using solution and/or solid phase peptide synthesis methods as disclosed in, for example, U.S. Pat. No. 5,120,830, the entire contents of which are incorporated herein by reference.

As used herein, the term "peptide analog" refers to a peptide which shares a common structural feature with the molecule to which it is deemed to be an analog. Peptide analogs include "unique fragments" which are related to, or derived from, functional domain(s) of E-cadherin, polymers of functional domain(s) or polymers of unique fragments of functional domain(s). A unique fragment of a protein or nucleic acid sequence can include a fragment which is not currently known to occur elsewhere in nature (except in allelic or allelomorphic variants). Unique fragments act as a "signature" of the gene or protein from which they are derived. A unique fragment will generally be at least about 9, 12, 15, 18, 21, 24, and 27 nucleotides, or 3, 4, 5, 6, 7, 8 and 9 amino acids in length, respectively.

In addition to the foregoing, tagged E-Cadherin peptides are encompassed in the present invention, for example, recombinant fusion protein fragments corresponding to specific amino acid regions of E-cadherin are commercially available. For example, E-cadherin peptide fragments corresponding to amino acids about 600-707 (AbCam); smaller synthetic peptides, such as S A L L L L L Q V S S W L (SEQ ID NO: 2), corresponding to amino acid residues 9-21 (MA1-06303), and the peptide P G F D A E S Y T F T V P R (SEQ ID NO: 3), corresponding to amino acid residues 30-43 (MA1-06304) from Affinity BioReagents. Also included are MA1-06301 and MA1-06302 immunogens (Affinity BioReagents), which are affinity purified ~80 kD extracellular fragments of E-cadherin derived from tryptic digestion of A-431 human vulva carcinoma cells. Antibodies to MA1-06302 detect an approximately 120 kDa E-cadherin protein. Furthermore, there is data demonstrating that cleavage of the 80-kDa extracellular domain of E-cadherin from the cell surface may provide an innate form of pathogen defense by acting as a decoy receptor. Fernanda da Silva et al., (2003) *Infect Immun.* 71(3): 1580-1583. Accordingly, commercially available E-cadherin peptides can be used in the methods describe herein. Alternatively, one of ordinary skill in the art can readily identify unique fragments by searching available computer databases of nucleic acid and protein sequences such as Genbank, (Los Alamos National Laboratories, USA), EMBL, or SWISS-PROT. A unique fragment is particularly useful, for example, in generating monoclonal antibodies or in screening genomic DNA or cDNA libraries.

It will be appreciated by those skilled in the art that various modifications of the foregoing peptide and or peptide analogs can be made without departing from the essential nature of the invention. For example, the peptides of the invention can be specifically reactive with a cadherin, e.g., an E-cadherin, and thereby preventing E-cadherin from binding to its cognate or ligand. Accordingly, it is intended that peptides include conservative substitutions, as well as those peptides coupled to other proteins and/or matrices, e.g., coupled to a solid support (e.g., polymeric bead, microtiter plates or beads), a carrier molecule (e.g., keyhole limpet hemocyanin), a toxin (e.g., ricin) or a reporter group (e.g., a radiolabel or other tag), are embraced within the teachings of the invention. These and other methods of coupling a peptide are known and available to one of ordinary skill in the art.

As used herein, the term "functionally equivalent peptide analog" refers to a peptide analog that retains function, for example, such an analog is capable of inhibiting the binding of an E-cadherin expressing cell in vitro by competing with E-cadherin for binding to another cell. Functionally equivalent peptide analogs of E-cadherin are identified, for example, in in vitro screening assays that measure the ability of the peptide analog to inhibit E-cadherin-mediated adhesion between cells. Such assays are predictive of the ability of a molecule to inhibit this adhesion in vivo. Accordingly, a "functionally equivalent peptide analog" of E-cadherin includes, but is not limited to, the extracellular domain of E-cadherin, fragments of the extracellular domain and peptide analogs of the extracellular domain, provided that the peptide fragments and analogs are capable of inhibiting adhesion between at least one E-cadherin expressing cell in vitro. As used herein, "conservative amino acid substitution" refers to an amino acid substitution which does not alter the relative charge or size characteristics of the peptide in which the amino acid substitution is made. Conservative substitutions of amino acids include substitutions made amongst the individual amino acids within the following groups: i) M, I, L and V; ii) F, Y, and W; iii) K, R, and H; iv) A and G; v) S and T; vi) Q and N; and vii) E and D.

Additionally, one skilled in the art can review structure-function studies identifying residues in similar polypeptides that are important for activity or structure. In view of such a comparison, the skilled artisan can predict the importance of amino acid residues in a protein that correspond to amino acid residues important for activity or structure in similar proteins. One skilled in the art may opt for chemically similar amino acid substitutions for such predicted important amino acid residues.

One skilled in the art can also analyze the three-dimensional structure and amino acid sequence in relation to that structure in similar polypeptides. In view of such information, one of ordinary skill in the art may predict the alignment of amino acid residues of a polypeptide with respect to its three dimensional structure. In certain embodiments, one skilled in the art may choose to not make radical changes to amino acid residues predicted to be on the surface of the protein, since such residues may be involved in important interactions with other molecules. Moreover, one skilled in the art may generate test variants containing a single amino acid substitution at each desired amino acid residue. The variants can then be screened using activity assays known in the art. Such variants can be used to gather information about suitable variants. For example, if one discovered that a change to a particular amino acid residue resulted in destroyed, undesirably reduced, or unsuitable activity, variants with such a change can be avoided. In other words, based on information gathered from such routine experiments, one skilled in the art can readily determine the amino acids where further substitutions should be avoided either alone or in combination with other mutations.

A number of scientific publications have been devoted to the prediction of secondary structure. See Moult, 1996, *Curr. Op. in Biotech.* 7:422-427; Chou et al, 1974, *Biochemistry* 13:222-245; Chou et al, 1974, *Biochemistry* 113:211-222; Chou et al, 1978, *Adv. Enzymol Relat. Areas Mol. Biol.* 47:45-148; Chou et al, 1979, *Ann. Rev. Biochem.* 47:251-276; and Chou et al, 1979, *Biophys. J.* 26:367-384. Moreover, computer programs are currently available to assist with predicting secondary structure. One method of predicting secondary structure is based upon homology modeling. For example, two polypeptides or proteins that have a sequence identity of greater than about 30%, or similarity greater than 40% often have similar structural topologies. The recent growth of the protein structural database has provided enhanced predictability of secondary structure, including the potential number of folds within a polypeptide's or protein's structure. See Holm et al, 1999, *Nucl. Acid. Res.* 27:244-247. It has been suggested (Brenner et al, 1997, *Curr. Op. Struct. Biol.* 7:369-376) that there are a limited number of folds in a given polypeptide or protein and that once a critical number of structures have been resolved, structural prediction will become dramatically more accurate.

Still, a peptide analog includes non-peptide drugs with properties analogous to those of the template peptide. These types of non-peptide compound are termed "peptide mimetics" or "peptidomimetics". See Fauchere, 1986, *Adv. Drug Res.* 15:29; Veber & Freidinger, 1985, *TINS* p. 392; and Evans et al., 1987, *J. Med. Chem.* 30:1229, which are incorporated herein by reference for any purpose. Such compounds are often developed with the aid of computerized molecular modeling. Peptide mimetics that are structurally similar to therapeutically useful peptides may be used to produce a similar therapeutic or prophylactic effect. Generally, peptidomimetics are structurally similar to a paradigm polypeptide (i.e., a polypeptide that has a biochemical property or pharmacological activity), such as human antibody, but have one or more peptide linkages optionally replaced by a linkage selected from: —CH2-NH—, —CH2-S—, —CH2-CH2-, —CH=CH-(cis and trans), —COCH2-, —CH(OH)CH2-, and —CH2SO—, by methods well known in the art. Systematic substitution of one or more amino acids of a consensus sequence with a D-amino acid of the same type (e.g., D-lysine in place of L-lysine) may be used in certain embodiments to generate more stable peptides. In addition, constrained peptides comprising a consensus sequence or a substantially identical consensus sequence variation may be generated by methods known in the art (Rizo & Gierasch, 1992, *Ann. Rev. Biochem.* 61:387, incorporated herein by reference for any purpose); for example, by adding internal cysteine residues capable of forming intramolecular disulfide bridges which cyclize the peptide.

As used herein, "a heterotypic cognate of E-cadherin" refers to a peptide or protein that is present in, or derived from a specific cell type, and which specifically recognizes and binds to E-cadherin, but is not the same cell type as the E-cadherin expressing cell. For example, Whittard et al. supra describe that $\alpha^E\beta_7$ integrin is an exemplary heterotypic cognate of E-cadherin. Heterotypic cognates of E-cadherin are useful as reagents in in vitro adhesion assays for screening molecular libraries. Such adhesion assays assess the ability of a molecule (e.g., a molecular library member) to modulate the interaction of two binding partners. Typically, the binding partners are cells which specifically bind to one another via a ligand-receptor mediated mechanism. The cell can be a cell which naturally expresses a binding partner, or can be a cell which is transfected or otherwise genetically altered to express the binding partner.

The agent or peptide described herein can also be a "ligand", which refers to any molecule that binds to another, e.g., a soluble molecule that binds to a receptor. A ligand as encompassed herein can be a heterotypic E-cadherin cognate, a functionally equivalent peptide fragment or analog of the isolated heterotypic E-cadherin cognate, or a cell extracellularly expressing the isolated heterotypic cognate or its functionally equivalent peptide fragment or analog. Simply, at least one ligand is E-cadherin. As used herein, a cell expressing E-cadherin on the cell surface also functions as a "receptor E-cadherin". Hence, a ligand as described herein binds to the receptor E-cadherin. In a preferred embodiment, the receptor binds selectively and/or specifically.

In some embodiments, the agent described herein includes a nucleic acid and its deduced amino acid sequence. For example, a nucleic acid which corresponds to the extracellular domain of E-cadherin, may be used in computer-based modeling systems to predict the secondary and tertiary structure of the extracellular domain. Such computer-based systems are well known to those of ordinary skill in the art of rational drug design. Based upon the tertiary structure of a receptor protein, it is often possible to identify a binding region which is involved in its biological activity. From this information, peptides or other compounds which include or mimic this structure and/or which are capable of binding to it can be rationally designed. In this way, new compounds may be designed which mimic the activity of the receptor or ligand or which will act as competitive inhibitors of the receptor or ligand.

Production of Definitive Endoderm

In some processes, differentiation to definitive endoderm is achieved by providing to the stem cell culture a growth factor of the TGFβ superfamily in an amount sufficient to promote differentiation to definitive endoderm. Growth factors of the TGFβ superfamily which are useful for the production of definitive endoderm are selected from the Nodal/Activin or BMP subgroups. In some preferred differentiation processes, the growth factor is selected from the group consisting of Nodal, activin A and activin B. Additionally, the growth factor Wnt3a and other Wnt family members are useful for the production of definitive endoderm cells. In certain differentiation processes, combinations of any of the above-mentioned growth factors can be used.

Also, as used herein, "exogenously added," compounds such as growth factors, differentiation factors, and the like, in the context of cultures or conditioned media, refers to growth factors that are added to the cultures or media to supplement any compounds or growth factors that may already be present in the culture or media. For example, growth factors of the invention include but are not limited to a "retinoid", which refers to retinol, retinal or retinoic acid as well as derivatives of any of these compounds. In a preferred embodiment, the retinoid is retinoic acid. A growth factor also includes a "FGF family growth factor," "a fibroblast growth factor" or "member of the fibroblast growth factor family" is meant an FGF selected from the group consisting of FGF1, FGF2, FGF3, FGF4, FGF5, FGF6, FGF7, FGF8, FGF9, FGF10, FGF11, FGF12, FGF13, FGF14, FGF15, FGF16, FGF17, FGF18, FGF19, FGF20, FGF21, FGF22 and FGF23. In some embodiments, "FGF family growth factor," "a fibroblast growth factor" or "member of the fibroblast growth factor family" means any growth factor having homology and/or function similar to a known member of the fibroblast growth factor family.

With respect to some of the processes for the differentiation of pluripotent stem cells to definitive endoderm cells, the above-mentioned growth factors are provided to the cells so that the growth factors are present in the cultures at concentrations sufficient to promote differentiation of at least a portion of the stem cells to definitive endoderm cells. In some processes, the above-mentioned growth factors are present in the cell culture at a concentration of at least about 5 ng/ml, at least about 10 ng/ml, at least about 25 ng/ml, at least about 50 ng/ml, at least about 75 ng/ml, at least about 100 ng/ml, at least about 200 ng/ml, at least about 300 ng/ml, at least about 400 ng/ml, at least about 500 ng/ml at least about 1000 ng/ml, at least about 2000 ng/ml, at least about 3000 ng/ml, at least about 4000 ng/ml, at least about 5000 ng/ml or more than about 5000 ng/ml.

In certain processes for the differentiation of pluripotent stem cells to definitive endoderm cells, the above-mentioned growth factors are removed from the cell culture subsequent to their addition. For example, the growth factors can be removed within about one day, about two days, about three days, about four days, about five days, about six days, about seven days, about eight days, about nine days or about ten days after their addition. In a preferred process, the growth factors are removed about four days after their addition.

Cultures of definitive endoderm cells can be produced from embryonic stem cells in medium containing reduced serum or no serum. Under certain culture conditions, serum concentrations can range from about 0.05% v/v to about 20% v/v. For example, in some differentiation processes, the serum concentration of the medium can be less than about 0.05% (v/v), less than about 0.1% (v/v), less than about 0.2% (v/v), less than about 0.3% (v/v), less than about 0.4% (v/v), less than about 0.5% (v/v), less than about 0.6% (v/v), less than about 0.7% (v/v), less than about 0.8% (v/v), less than about 0.9% (v/v), less than about 1% (v/v), less than about 2% (v/v), less than about 3% (v/v), less than about 4% (v/v), less than about 5% (v/v), less than about 6% (v/v), less than about 7% (v/v), less than about 8% (v/v), less than about 9% (v/v), less than about 10% (v/v), less than about 15% (v/v) or less than about 20% (v/v). In some processes, definitive endoderm cells are grown without serum or without serum replacement. In still other processes, definitive endoderm cells are grown in the presence of B27. In such processes, the concentration of B27 supplement can range from about 0.1% v/v to about 20% v/v. In other embodiments, the definitive endoderm cells are grown in the absence of B27.

In some processes for differentiating human definitive endoderm cells from hESCs, differentiation is initiated in the absence of serum and in the absence of insulin and/or insulin-like growth factor. During the course of differentiation, the serum concentration may be gradually increased in order to promote adequate cell survival. In preferred embodiments, differentiation of hESCs to definitive endoderm cells is initiated in the absence of serum and in the absence of any supplement comprising insulin or insulin-like growth factors. The absence of serum and absence of supplement comprising insulin or insulin-like growth factors is maintained for about 1 to about 2 days, after which, serum is gradually added to the differentiating cell culture over the course of differentiation. In preferred embodiments, the concentration of serum does not exceed about 2% during the course of differentiation.

Definitive endoderm cell cultures and cell populations as well as detailed processes for the production of definitive endoderm cells from embryonic stem cells are further described in U.S. patent application Ser. No. 11/021,618, entitled DEFINITIVE ENDODERM, filed Dec. 23, 2004 and U.S. patent application Ser. No. 11/317,387, entitled EXPANSION OF DEFINITIVE ENDODERM CELLS, filed Dec. 22, 2005, the disclosures of which are incorporated herein by reference in their entireties.

Methods for Increasing Definitive Endoderm Production and/or Increasing Production of hESC-Derived Cell Population As used herein, "derived from hESCs," "produced from hESCs," "differentiated from hESCs" and/or "hESC-derived cell population" or equivalent expressions refer to the production of a differentiated cell type from hESCs in vitro rather than in vivo.

One embodiment of the present invention relates to an in vitro method for increasing definitive endoderm production by providing an agent to a cell culture comprising E-cadherin-expressing human embryonic stem cells. In such embodiments, the agent inhibits adhesion of the E-cadherin-expressing cells to each other. Under such conditions, the E-cadherin-expressing human embryonic stem cells are then differentiated by contacting the cells with a medium comprising a growth factor of the Nodal/Activin subgroup of the TGFβ superfamily of growth factors. As compared to identically or similarly differentiated human embryonic cell cultures that have not been contacted with the agent, the production of definitive endoderm will have been increased in the cultures having been contacted with the agent.

In some embodiments, the agent that is used binds to E-cadherin. As described further below, in certain preferred embodiments, the agent selectively and/or specifically binds to E-cadherin and acts so as to antagonize the E-cadherin adhesion function. In other preferred embodiments, the E-cadherin antagonist is a peptide or a peptide analog. For example, the peptide can be an E-cadherin peptide corresponding to an E-cadherin extracellular domain at amino acid residues 600-700 of human E-cadherin (SEQ ID NO:1).

Other embodiments of the present invention relate to in vitro methods for increasing the production of definitive endoderm as described above wherein the provided agent is a metal ion chelator. In a preferred embodiment, the metal ion chelator is a calcium ion chelator. Calcium ion chelators are able to bind calcium in a selective way. That is, the calcium chelators have higher affinity for calcium than for any other metal ions. Binding to calcium is performed through carboxylic groups, so it can be affected by pH, other ions or co-ordination to proteins, lipids, etc. The process is a reversible equilibrium. The calcium, chelator and complex concentrations are related by a dissociation constant, $K_d=([Ca^{2+}]\cdot[Chelator])/[\{Chelator-Ca\}_{complex}]$. When the $K_d$ is very low, it is a high-affinity chelator (i.e., the chelator has a high tendency to bind calcium). If the $K_d$ is high (μM or higher), it is a low-affinity chelator. Preferred calcium chelators include, ethylenediaminetetraacetic acid (EDTA) and ethyleneglycoltetraacetic acid (EGTA); however, it will be appreciated that other metal ion chelators, such as those selected from the group consisting of 1,10 phenanthroline, diethylenetriaminepentaacetate (DTPA), hydroxyethylethylenediaminetriacetic acid (HEEDTA), diaminocyclohexanetetraacetic acid (CDTA), 1,2-Bis(2-aminophenoxy)ethane-N,N,N',N'-tetraacetic acid (BAPTA) can also be used. Furthermore, combinations of such chelators and salts of such chelators can also be used. Example 3 describes directed differentiation of DE from hESCs in the presence of EDTA. The presence of EDTA in the culture media reduces the concentration of $Ca^{2+}$ ions present. More selective chelation of $Ca^{2+}$ can be achieved by using EGTA. Similar methods of chelating or binding or capturing calcium ions, extra- or intra-cellularly, using other calcium chelators is well known to one skilled in the art. High-affinity chelators trap calcium efficiently and the calcium chelators described herein are only illustrative examples and are not meant to be limiting. Binding of calcium disrupts E-cadherin function, which decreases cell-cell binding and/or affects cell signaling.

In some embodiments of the present invention, the step of providing the agent to the E-cadherin-expressing human embryonic stem cells and the differentiation step can be performed in the same medium. However, in preferred embodiments, the E-cadherin-expressing human embryonic stem cells are provided with the agent in a first medium and then differentiated in a second medium. In some embodiments, the first medium is different from the second medium. In other embodiments, the first medium is the same as the second medium except that the second medium does not comprise exogenously added agent.

In still other embodiments of the invention, there is provided an in vitro method for increasing definitive endoderm production and/or increasing production of a cell derived from a human embryonic stem cell (hESC) by contacting an agent with a human embryonic stem cell (hESC) culture in a first medium, wherein the culture comprises at least one E-cadherin expressing cell, and wherein the agent selectively binds to E-cadherin on the E-cadherin expressing cell and inhibits adhesion of the E-cadherin expressing cell to another cell; and differentiating the hESC culture in a second medium comprising a growth factor of the Nodal/Activin subgroup of the TGFβ superfamily, thereby increasing definitive endoderm production and/or production of a cell derived from a human embryonic stem cell (hESC).

Accordingly, in one aspect of the invention, the agent capable of selectively binding or specifically binding to an E-cadherin expressing cell is an E-cadherin polyclonal or a monoclonal antibody. As used herein, the term "selectively binds" or "specifically binds," when used in reference to an antibody and an antigen or epitopic portion thereof, means that the antibody and the antigen (or epitope) have a dissociation constant of at least about $1\times10^{-7}$, generally at least about $1\times10^{-8}$, usually at least about $1\times10^{-9}$, and particularly at least about $1\times10^{-10}$ or less. Methods for identifying and selecting an antibody having a desired specificity are well known and routine in the art (see, for example, Harlow and Lane, "Antibodies: A Laboratory Manual" (Cold Spring Harbor Pub. 1988), which is incorporated herein by reference.

Methods for producing antibodies those can selectively and specifically bind to one or more E-cadherin polypeptide epitopes, particularly epitopes unique to an E-cadherin polypeptide or peptide (e.g., signature or unique sequences), are disclosed herein or are otherwise well known and routine in the art. Such antibodies can be polyclonal antibodies or monoclonal antibodies (mAbs), and can be humanized or chimeric antibodies, single chain antibodies, anti idiotypic antibodies, and epitope-binding fragments of any of the above, including, for example, Fab fragments, F(ab')2 fragments or fragments produced by a Fab expression library. Such antibodies can be used, for example, in the detection of E-cadherin polypeptides, or mutant E-cadherin polypeptides, including variant E-cadherin polypeptides, which can be in a biological sample, or can be used for the inhibition of abnormal E-cadherin activity. Thus, the antibodies can be utilized to inhibit E-cadherin binding and decrease or inhibit cellular adhesion and thereby increase directed differentiation of hESCs.

For the production of antibodies that bind to E-cadherin, including an E-cadherin variant or E-cadherin mutant, various host animals can be immunized by injection with an E-cadherin polypeptide, mutant polypeptide, variant, or a portion thereof. Such host animals can include but are not limited to, rabbits, mice, and rats. Various adjuvants can be used to increase the immunological response, depending on the host species, including, but not limited to, Freund's (complete and incomplete), mineral gels such as aluminum hydroxide, surface active substances such as lysolecithin, pluronic polyols, polyanions, peptides, oil emulsions, keyhole limpet hemocyanin, dinitrophenol, and potentially useful human adjuvants such as BCG (Bacillus Calmette-Guerin) or *Corynebacterium parvum*.

Antibodies that bind to an E-cadherin polypeptide, or peptide portion thereof or to a variant or mutant peptide, of the invention can be prepared using an intact polypeptide or fragments containing small peptides of interest as the immunizing antigen, e.g., LDRE (amino acids 220-223 of SEQ ID NO: 1), DXNDN (amino acids 367-371 of SEQ ID NO: 1), DXNDNXP (amino acids 367-373 of SEQ ID NO: 1), HAV, and the like (FIG. 1). The polypeptide or a peptide used to immunize an animal can be derived from translated cDNA or chemical synthesis, and can be conjugated to a carrier protein, if desired. Such commonly used carriers that can be chemically coupled to the peptide include keyhole limpet hemocyanin, thyroglobulin, bovine serum albumin, tetanus toxoid and others as described above or otherwise known in the art. The coupled polypeptide or peptide is then used to immunize the animal and antiserum can be collected. If desired, polyclonal or monoclonal antibodies can be purified, for example, by binding to and elution from a matrix to which the polypeptide or a peptide to which the antibodies were raised is bound. Any of various techniques commonly used in immunology for purification and/or concentration of polyclonal antibodies, as well as monoclonal antibodies, can be used (see for example, Coligan, et al., Unit 9, Current Protocols in Immunology, Wiley Interscience, 1991, which is incorporated herein by reference).

Anti-idiotype technology can be used to produce monoclonal antibodies that mimic an epitope. For example, an anti-idiotypic monoclonal antibody made to a first monoclonal antibody will have a binding domain in the hyper variable region that is the image of the epitope bound by the first monoclonal antibody. Antibodies of the invention include polyclonal antibodies, monoclonal antibodies, and fragments of polyclonal and monoclonal antibodies that specifically bind to a mutant E-cadherin polypeptide or peptide portion thereof.

The preparation of polyclonal antibodies is well known to those skilled in the art (see, for example, Green et al., Production of Polyclonal Antisera, in Immunochemical Protocols (Manson, ed.), pages 1-5 (Humana Press 1992); Coligan et al., Production of Polyclonal Antisera in Rabbits, Rats, Mice and Hamsters, in Current Protocols in Immunology, section 2.4.1 (1992), which are incorporated herein by reference). The preparation of monoclonal antibodies likewise is conventional (see, for example, Kohler and Milstein, Nature, 256:495, 1975, which is incorporated herein by reference; see, also Coligan et al., supra, sections 2.5.1-2.6.7). Briefly, monoclonal antibodies can be obtained by injecting mice with a composition comprising an antigen, verifying the presence of antibody production by removing a serum sample, removing the spleen to obtain B lymphocytes, fusing the B lymphocytes with myeloma cells to produce hybridomas, cloning the hybridomas, selecting positive clones that produce antibodies to the antigen, and isolating the antibodies from the hybridoma cultures.

Monoclonal antibodies can be isolated and purified from hybridoma cultures by a variety of well-established techniques. Such isolation techniques include affinity chromatography with Protein-A Sepharose, size-exclusion chromatography, and ion-exchange chromatography (see Coligan et al., sections 2.7.1-2.7.12 and sections 2.9.1-2.9.3; Barnes et al., Purification of Immunoglobulin G (IgG), in Methods in Molecular Biology, Vol. 10, pages 79-104 (Humana Press 1992)). Methods of in vitro and in vivo multiplication of hybridoma cells expressing monoclonal antibodies are well-known to those skilled in the art. Multiplication in vitro can be carried out in suitable culture media such as Dulbecco's Modified Eagle Medium (DMEM) or RPMI 1640 medium, optionally supplemented by a mammalian serum such as fetal calf serum or trace elements and growth-sustaining supplements such as normal mouse peritoneal exudate cells, spleen cells, bone marrow macrophages. Production in vitro provides relatively pure antibody preparations and allows scale-up to yield large amounts of the desired antibodies. Large scale hybridoma cultivation can be carried out by homogenous suspension culture in an airlift reactor, in a continuous stirrer reactor, or in immobilized or entrapped cell culture. Multiplication in vivo can be carried out by injecting cell clones into mammals histocompatible with the parent cells, e.g., syngeneic mice, to cause growth of antibody-producing tumors. Optionally, the animals are primed with a hydrocarbon, especially oils such as pristane tetramethylpentadecane prior to injection. After one to three weeks, the desired monoclonal antibody is recovered from the body fluid of the animal.

In some embodiments, antibodies of the present invention can be derived from subhuman primate antibodies. General techniques for raising therapeutically useful antibodies in baboons can be found, for example, in Goldenberg et al., International Application Publication No. WO 91/11465, 1991; Losman et al., Int. J. Cancer, 46:310, 1990, which are incorporated herein by reference.

An E-cadherin antibody can also be derived from a "humanized" monoclonal antibody. Humanized monoclonal antibodies are produced by transferring mouse complementarity determining regions from heavy and light variable chains of the mouse immunoglobulin into a human variable domain, and then substituting human residues in the framework regions of the murine counterparts. The use of antibody components derived from humanized monoclonal antibodies obviates potential problems associated with the immunogenicity of murine constant regions. General techniques for cloning murine immunoglobulin variable domains are described, for example, by Orlandi et al., Proc. Natl. Acad. Sci. USA 86:3833, 1989, which is incorporated herein by reference. Techniques for producing humanized monoclonal antibodies are described, for example, by Jones et al., Nature, 321:522, 1986; Riechmann et al., Nature 332:323, 1988; Verhoeyen et al., Science 239:1534, 1988; Carter et al., Proc. Natl. Acad. Sci. USA, 89:4285, 1992; Sandhu, Crit. Rev. Biotech. 12:437, 1992; and Singer et al., J. Immunol. 150:2844, 1993, which are incorporated herein by reference.

Antibodies of the invention also can be derived from human antibody fragments isolated from a combinatorial immunoglobulin library (see, for example, Barbas et al., Methods: A Companion to Methods in Enzymology, Vol. 2, page 119, 1991; Winter et al., Ann. Rev. Immunol. 12:433, 1994, which are incorporated herein by reference). Cloning and expression vectors that are useful for producing a human immunoglobulin phage library can be obtained.

In addition, antibodies of the present invention can be derived from a human monoclonal antibody. Such antibodies are obtained from transgenic mice that have been "engineered" to produce specific human antibodies in response to antigenic challenge. In this technique, elements of the human heavy and light chain loci are introduced into strains of mice derived from embryonic stem cell lines that contain targeted disruptions of the endogenous heavy and light chain loci. The transgenic mice can synthesize human antibodies specific for human antigens, and the mice can be used to produce human antibody-secreting hybridomas. Methods for obtaining human antibodies from transgenic mice are described by Green et al., Nature Genet., 7:13 (1994); Lonberg et al., Nature, 368:856 (1994); Taylor et al., Int. Immunol., 6:579 (1994), each of which is incorporated herein by reference.

Antibody fragments of the invention can be prepared by proteolytic hydrolysis of an antibody or by expression in E. Coli of DNA encoding the fragment. Antibody fragments can be obtained by pepsin or papain digestion of whole antibodies by conventional methods. For example, antibody fragments can be produced by enzymatic cleavage of antibodies with pepsin to provide a 5S fragment denoted $F(ab')_2$. This fragment can be further cleaved using a thiol reducing agent, and optionally a blocking group for the sulfhydryl groups resulting from cleavage of disulfide linkages, to produce 3.5S Fab' monovalent fragments. Alternatively, an enzymatic cleavage using pepsin produces two monovalent Fab' fragments and an Fc fragment directly. These methods are described, for example, by Goldenberg, U.S. Pat. Nos. 4,036,945 and 4,331,647, and references contained therein, each of which in incorporated herein by reference (see, also, Nisonhoff et al., Arch. Biochem, Biophys., 89:230, 1960; Porter, Biochem. J. 73:119, 1959; Edelman et al., Meth. Enzymol. 1:422, 1967; and Coligan et al., at sections 2.8.1-2.8.10 and 2.10.1-2.10.4). Other methods of cleaving antibodies, such as separation of heavy chains to form monovalent light-heavy chain fragments, further cleavage of fragments, or other enzymatic, chemical, or genetic techniques can also be used, provided the fragments bind to the antigen that is recognized by the intact antibody.

Fv fragments comprise an association of VH and VL chains, for example, which can be noncovalent (see Inbar et al., *Proc. Natl. Acad. Sci. USA* 69:2659, 1972). The variable chains also can be linked by an intermolecular disulfide bond, can be crosslinked by a chemical such as glutaraldehyde (Sandhu, supra, 1992), or Fv fragments comprising VH and VL chains can be connected by a peptide linker. These single chain antigen binding proteins (sFv) are prepared by constructing a structural gene comprising DNA sequences encoding the VH and VL domains connected by an oligonucleotide. The structural gene is inserted into an expression vector, which is subsequently introduced into a host cell such as *E. coli*. The recombinant host cells synthesize a single polypeptide chain with a linker peptide bridging the two V domains. Methods for producing sFvs are described, for example, by Whitlow et al., Methods: A Companion to Meth. Enzymol., 2:97, 1991; Bird et al., *Science* 242:423, 1988; Ladner et al., U.S. Pat. No. 4,946,778; Pack et al., *BioTechnology* 11: 1271, 1993; and Sandhu, supra, 1992).

Another form of an antibody fragment is a peptide coding for a single complementarity determining region (CDR). CDR peptides ("minimal recognition units") can be obtained by constructing genes encoding the CDR of an antibody of interest. Such genes are prepared, for example, by using the polymerase chain reaction to synthesize the variable region from RNA of antibody-producing cells. See, for example, Larrick et al., Methods: *A Companion to Meth. Enzymol.*, 2:106, (1991).

The above methods are merely illustrative and other methods of antibody production are known in the art and available to one of ordinary skill in the art, which methods are embodied in the present invention.

Methods of Monitoring the Production of Definitive Endoderm and/or a hESC-Derived Cell Population Also provided herein, is a method of monitoring the production of definitive endoderm and/or a hESC-derived cell population. As hESCs differentiate to definitive endoderm they down regulate E-cadherin and transition from an epithelial epiblast state to a mesenchymal definitive endoderm cell (D'Amour et al. *Nat. Biotech.* 23, 1534-1541, (2005)). The progression of the hESC culture to definitive endoderm can be monitored by determining the expression of markers characteristic of definitive endoderm. In some processes, the expression of certain markers is determined by detecting the presence or absence of the marker. Alternatively, the expression of certain markers can be determined by measuring the level at which the marker is present in the cells of the cell culture or cell population. In such processes, the measurement of marker expression can be qualitative or quantitative. One method of quantitating the expression of markers that are produced by marker genes is through the use of quantitative PCR (Q-PCR). Methods of performing Q-PCR are well known in the art. Other methods which are known in the art can also be used to quantitate marker gene expression. For example, the expression of a marker gene product can be detected by using antibodies specific for the marker gene product of interest. In certain processes, the expression of marker genes characteristic of definitive endoderm as well as the lack of significant expression of marker genes characteristic of hESCs and other cell types is determined.

As described further in the Examples below, the definitive endoderm cells produced by the processes described herein express the CXCR4 and CER marker gene, thereby producing the CXCR4 and CER gene product. As explained in our previous U.S. patent application Ser. No. 11/021,618, the principal markers defining the early DE cell include but are not limited to FOXA2, CER, GSC, N-cadherin, CXCR4 and SOX17, and by the absence of significant expression of certain other markers, such as SOX1, SOX7, thrombomodulin (TM), SPARC and alpha fetoprotein (AFP) [D'Amour et al. 2005 supra]. Other markers of definitive endoderm are MIXL1, GATA4, HNF3b, GSC, FGF17, VWF, CALCR, FOXQ1, CMKOR1 and CRIP1.

As stated above, at least one marker of definitive endoderm is the CXCR4 gene. The CXCR4 gene encodes a cell surface chemokine receptor whose ligand is the chemoattractant SDF-1. The principal roles of the CXCR4 receptor in the adult are believed to be the migration of hematopoetic cells to the bone marrow, lymphocyte trafficking and the differentiation of various B cell and macrophage blood cell lineages [Kim, C., and Broxmeyer, H. J. *Leukocyte Biol.* 65, 6-15 (1999)]. The CXCR4 receptor also functions as a co-receptor for the entry of HIV-1 into T-cells [Feng, Y., et al. *Science,* 272, 872-877 (1996)]. In an extensive series of studies [McGrath, K. E. et al. *Dev. Biology* 213, 442-456 (1999)], the expression of the chemokine receptor CXCR4 and its unique ligand, SDF-1 [Kim, C., and Broxmyer, H., J. *Leukocyte Biol.* 65, 6-15 (1999)], were delineated during early development and adult life in the mouse. The CXCR4/SDF1 interaction in development became apparent when it was demonstrated that if either gene was disrupted in transgenic mice [Nagasawa et al. *Nature,* 382, 635-638 (1996)], Ma, Q., et al *Immunity,* 10, 463-471 (1999)] it resulted in late embryonic lethality. McGrath et al. demonstrated that CXCR4 is the most abundant chemokine receptor messenger RNA detected during early gastrulating embryos (E7.5) using a combination of RNase protection and in situ hybridization methodologies. In the gastrulating embryo, CXCR4/SDF-1 signaling appears to be mainly involved in inducing migration of primitive-streak germ layer cells and is expressed by definitive endoderm, mesoderm and extraembryonic mesoderm present at this time. In E7.2-7.8 mouse embryos, CXCR4 and alpha-fetoprotein are mutually exclusive indicating a lack of CXCR4 expression in visceral endoderm [McGrath, K. E. et al. *Dev. Biology* 213, 442-456 (1999)].

Since DE cells produced by differentiating pluripotent cells express the CXCR4 marker gene, expression of CXCR4 can be monitored in order to track the production of definitive endoderm cells. Additionally, definitive endoderm cells produced by the methods described herein express other markers of definitive endoderm including, but not limited to, SOX17, MIXL1, GATA4, HNF3b, GSC, FGF17, VWF, CALCR, FOXQ1, CER, CMKOR1 and CRIP1. In other processes, expression of the both the CXCR4 marker gene and the OCT4 marker gene, is monitored. Additionally, because DE cells express the CXCR4 marker gene at a level higher than that of the AFP, SPARC or Thrombomodulin (TM) marker genes, the expression of these genes can also be monitored and requires no more experimentation that that described herein.

It will be appreciated that expression of CXCR4 in endodermal cells does not preclude the expression of SOX17. As such, definitive endoderm cells produced by the processes described herein will substantially express SOX17 and CXCR4 but will not substantially express AFP, TM, SPARC or PDX1.

Still, various methods can be utilized for quantifying the presence of the selected markers. For measuring the amount of a molecule that is present, a convenient method is to label a molecule with a detectable moiety, which may be fluorescent, luminescent, radioactive, enzymatically active, etc., particularly a molecule specific for binding to the parameter with high affinity. Fluorescent moieties are readily available for labeling virtually any biomolecule, structure, or cell type. Immunofluorescent moieties can be directed to bind not only to specific proteins but also specific conformations, cleavage products, or site modifications like phosphorylation. Individual peptides and proteins can be engineered to autofluoresce, e.g. by expressing them as green fluorescent protein chimeras inside cells (for a review see Jones et al. (1999) Trends Biotechnol. 17(12):477 81). Thus, antibodies can be genetically modified to provide a fluorescent dye as part of their structure. Depending upon the label chosen, parameters may be measured using other than fluorescent labels, using such immunoassay techniques as radioimmunoassay (RIA) or enzyme linked immunosorbance assay (ELISA), homogeneous enzyme immunoassays, and related non-enzymatic techniques. The quantitation of nucleic acids, especially messenger RNAs, is also of interest as a parameter. These can be measured by hybridization techniques that depend on the sequence of nucleic acid nucleotides. Techniques include polymerase chain reaction methods as well as gene array techniques. See, for example, Current Protocols in Molecular Biology, Ausubel et al., eds, John Wiley & Sons, New York, N.Y., 2000; Freeman et al. (1999) *Biotechniques* 26(1):112 225; Kawamoto et al. (1999) *Genome Res* 9(12):1305 12; and Chen et al. (1998) *Genomics* 51(3):313 24.

Compositions of Human Embryonic Stem Cells In Vitro

One embodiment of the present invention relates to an in vitro composition comprising an antagonist of E-cadherin specifically bound to an E-cadherin-expressing human embryonic stem cells. In such compositions, the binding of the antagonist inhibits adhesion between the embryonic stem cells. Accordingly, compositions of the present invention include human embryonic stem cell cultures wherein at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95% or at least greater than 95% of the human embryonic stem cells are not adhered to other human embryonic stem cells in the cell culture. The proportion of cells adhered to other cells in the culture depends on, among other things, the antagonistic efficacy and the concentration of the agent supplied to the cell culture. In a preferred embodiment, the antagonist is a polyclonal or a monoclonal E-cadherin antibody.

Other embodiments of the present invention included cell cultures comprising a calcium-binding agent and E-cadherin-expressing human embryonic stem cells in a culture medium. In such cultures, the calcium-binding agent is bound to calcium ions in the culture medium, thereby inhibiting adhesion between the embryonic stem cells. Accordingly, compositions of the present invention include human embryonic stem cell cultures wherein at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95% or at least greater than 95% of the human embryonic stem cells are not adhered to other human embryonic stem cells in the cell culture. In preferred embodiments, the calcium binding agent is selected from the group consisting of ethylenediaminetetraacetic acid (EDTA), ethyleneglycoltetraacetic acid (EGTA), 1,10 phenanthroline, diethylenetriaminepentaacetate (DTPA), hydroxyethylethylenediaminetriacetic acid (HEEDTA), diaminocyclohexanetetraacetic acid (CDTA), 1,2-Bis(2-aminophenoxy)ethane-N,N,N',N'-tetraacetic acid (BAPTA), and pharmaceutically acceptable salts thereof.

Methods for Identifying an E-Cadherin an Agent Capable of Increasing Production of Cell Derived from a Human Embryonic Stem Cell Some embodiments of the present invention relate to methods for identifying an agent capable of increasing production of a cell derived from a human embryonic stem cell. In these embodiments, a candidate agent is provided to a human embryonic stem cell culture. The human embryonic stem cell culture is then differentiated in a culture medium comprising a differentiation factor known to be capable of promoting the differentiation of said human embryonic stem cells. For example, human embryonic stem cells can be differentiated to definitive endoderm in medium lacking insulin like growth factor receptor agonists (or containing low levels of such molecules) and in the presence of activin A. Other factors capable of promoting the differentiation of human embryonic stem cells are known in the art. After differentiation has occurred, it can be determined whether the candidate agent increases the production of cells differentiated from the human embryonic stem cells by comparing the production of differentiated cells in the cell culture provided with the candidate agent to the production of differentiated cells in a human embryonic stem cell culture that has not been provided with the candidate agent but which has been treated with the same differentiation factor (differentiated under substantially the same conditions) as the cell culture provided with the candidate agent. Greater production of differentiated cells in the cell culture provided with the candidate agent as compared to the production of differentiated cells in the cell culture not provided with the candidate agent indicates that the candidate agent increases the production of a cell derived from a human embryonic cell.

In some embodiments of the present invention, candidate agents can be obtained from combinatorial synthetic chemical libraries. Generation of combinatorial synthetic chemical libraries is well known in the art. Alternatively, a natural product chemical library or a library of biological molecules generated by recombinant DNA or cell extraction processes can be utilized to obtain candidate agents. Procedures for generating each of the above libraries are routine in the art.

In another embodiment of the invention, there is provided a method for identifying an agent capable of increasing production of a cell derived from a human embryonic stem cell (hESC) by contacting a hESC in the presence of an agent in a culture medium, wherein the agent binds to extracellular calcium ions in the medium; differentiating the hESC culture in the culture; measuring production of the differentiated cell in the presence of the agent, wherein production of the differentiated cell in the presence of the agent is increased as compared to production of the differentiated cell in the absence of the agent, thereby indicating an agent capable of increasing production of a human embryonic derived cell.

Methods for Screening for Agonists and/or Antagonists of E-Cadherin

The present invention also provides a method for identifying an E-cadherin agonist or antagonist by providing a peptide library based on hESCs and an E-cadherin peptide; screening said peptide library for agents having high affinity binding to the E-cadherin peptide; and selecting a member of the peptide library binding to the E-cadherin peptide wherein the affinity of the member is equivalent or higher than that of a native homotypic E-cadherin peptide.

Human ES cells are useful for in vitro assays and screening to detect agents that affect hESC cellular adhesion and increase production of definitive endoderm. A wide variety of assays may be used for this purpose, including toxicology testing, immunoassays for protein binding; determination of cell growth, differentiation and functional activity; production of hormones; and the like.

Agents of interest for screening include known and unknown compounds that encompass numerous chemical classes, primarily organic molecules (e.g., polypeptides, peptides, peptide analogs, peptide variants and/or mutants), which may include organometallic molecules, inorganic molecules, genetic sequences, etc. In addition to complex biological agents, candidate agents include organic molecules comprising functional groups necessary for structural interactions, particularly hydrogen bonding, and typically include at least an amine, carbonyl, hydroxyl or carboxyl group, frequently at least two of the functional chemical groups. The candidate agents often comprise cyclical carbon or heterocyclic structures and/or aromatic or polyaromatic structures substituted with one or more of the above functional groups. Candidate agents are also found among biomolecules, including peptides, polynucleotides, saccharides, fatty acids, steroids, purines, pyrimidines, derivatives, structural analogs or combinations thereof.

Agents which are useful for modulation of cellular adhesion include but are not limited to agonists and/or antagonists that bind to the receptor E-cadherin or E-cadherin. As used herein, the term "agonist" refers to an agent or analog that binds productively to a receptor and mimics its biological activity. The term "antagonist" refers to an agent that binds to receptors but does not provoke the normal biological response. An agent as described herein in detail includes polypeptides, peptides and functional fragments or portions thereof, and as described above.

Compounds, including candidate agents, are obtained from a wide variety of sources including libraries of synthetic or natural compounds. For example, numerous means are available for random and directed synthesis of a wide variety of organic compounds, including biomolecules, expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs.

Agents are screened for biological activity by adding the agent to at least one and usually a plurality of cell samples, usually in conjunction with cells lacking the agent. The change in parameters in response to the agent is measured, and the result evaluated by comparison to reference cultures, e.g. in the presence and absence of the agent, obtained with other agents, etc.

The agents are conveniently added in solution, or readily soluble form, to the medium of cells in culture. The agents may be added in a flow-through system, as a stream, intermittent or continuous, or alternatively, adding a bolus of the compound, singly or incrementally, to an otherwise static solution. In a flow-through system, two fluids are used, where one is a physiologically neutral solution, and the other is the same solution with the test compound added. The first fluid is passed over the cells, followed by the second. In a single solution method, a bolus of the test compound is added to the volume of medium surrounding the cells. The overall concentrations of the components of the culture medium should not change significantly with the addition of the bolus, or between the two solutions in a flow through method.

Preferred agent formulations do not include additional components, such as preservatives, that may have a significant effect on the overall formulation. Thus preferred formulations consist essentially of a biologically active compound and a physiologically acceptable carrier, e.g. water, ethanol, DMSO, etc. However, if a compound is liquid without a solvent, the formulation may consist essentially of the compound itself.

A plurality of assays may be run in parallel with different agent concentrations to obtain a differential response to the various concentrations. As known in the art, determining the effective concentration of an agent typically uses a range of concentrations resulting from 1:10, or other log scale, dilutions. The concentrations may be further refined with a second series of dilutions, if necessary. Typically, one of these concentrations serves as a negative control, i.e. at zero concentration or below the level of detection of the agent or at or below the concentration of agent that does not give a detectable change in the phenotype.

Having generally described this invention, a further understanding can be obtained by reference to certain specific examples which are provided herein for purposes of illustration only, and are not intended to be limiting.

EXAMPLE 1

Disruption of Cellular Adherance of Pluripotent Cells Increases Production of Definitive Endoderm Human embryonic stem cells (hESCs; CyT203) were differentiated in vitro to definitive endoderm (DE) for about 2-3 days substantially as described in D'Amour et al. 2005 *Nat. Biotechnol.* 23:1534-41, D'Amour et al. 2006 *Nat Biotechnol.* 24(11):1392-401 and U.S. Patent Application Publication Number 2007/0154984, which are herein incorporated in their entireties. Briefly, undifferentiated human embryonic stem (hES) cells were maintained on mouse embryo fibroblast feeder layers (Specialty Media) in DMEM/F12 (Mediatech) supplemented with 20% KnockOut serum replacement (Gibco), 1 mM nonessential amino acids (Gibco), Glutamax (Gibco), penicillin/streptomycin (Gibco), 0.55 mM 2-mercaptoethanol (Gibco) and 4 ng/ml recombinant human FGF2 (R&D Systems). Activin A was added to the growth culture medium at 10-25 ng/ml to help maintain undifferentiated growth. Cultures were manually passaged at 1:4 1:10 split ratio every 5-7 days. Before initiating differentiation, hES cells were given a brief wash in PBS+/+ (Gibco). Cells were differentiated in RPMI (Mediatech) supplemented with Glutamax, penicillin/streptomycin, 100 ng/mL activin A and varying concentrations of defined FBS (HyClone). Additionally, 0.2% BSA and 25 ng/mL Wnt3a was added on the first day (d1) of differentiation. In most differentiation experiments FBS concentrations were 0% for the first 24 h, 0.2% for the second 24 h, and 0.2% for the third 24 h. Recombinant human activin A and Wnt3a were purchased from R&D Systems. Three 60 mm plates were utilized. One plate was treated with a mouse anti-human E-cadherin antibody (Zymed Cat. No. 13-1700) at 5 μg/mL for the first day (d1) and cultured for 3 days. The other two plates received no E-cadherin antibody treatment (controls). After the three (3) day treatment, hES-derived cells were dissociated using either TrypLE (Invitrogen #12563-011) or Accutase (Innovative Cell Technologies #AT104) at 37° C. The cells were washed in PBS with 10%

FBS to remove enzyme. Cells were pelleted and resuspended in PBS with 3% FBS (buffer) to block nonspecific antibody binding. Cells were labeled with CXCR4-PE conjugated antibody (R&D Systems) at 10 μL per approximately 1×10$^6$ cells for 20 minutes at room temperature. Cells were washed in buffer and resuspended in buffer at approx. 3-5×10$^6$ cells/ml. Cells were analyzed using a FACSCalibur (BD Bioscience).

As described in D'Amour et al. 2005 and U.S. Patent Application Publication No. 2007/0154984 supra, CXCR4 expression permits isolation of definitive endoderm. The chemokine receptor CXCR4 is expressed in the definitive endoderm and mesoderm but not in primitive endoderm/visceral endoderm. It was previously shown that hES-derived cell cultures exposed to activin A and lower levels of FBS have an increase in CXCR4 mRNA, which corresponds to the increase in other definitive endoderm markers, for example, see FIG. 5 of D'Amour et al. The percentage of CXCR4 positive cells in the two plates not receiving E-cadherin antibody treatment was approximately 70% and 76% (FIGS. 2A and 2B, respectively). In contrast, the plate receiving the E-cadherin antibody treatment had approximately 93% CXCR4 positive cells (FIG. 1C). Approximately 25,000 cells were analyzed per sample.

In view of the foregoing data, treatment of hESCs with an agent that binds E-cadherin on an E-cadherin expressing cell increases the efficiency of definitive endoderm production of the E-cadherin cell in the presence of strong nodal agonists, for example, Activin A.

EXAMPLE 2

Anti-Human E-Cadherin Treatment Increases the Expression of Definitive Endoderm Cell Surface Markers Cell cultures and culture conditions were substantially similar to those described above in Example 1 and in D'Amour et al. 2005 supra, including addition of 0.2% BSA. Nine tissue culture plates (35 mm) of hESCs (CyT203) were differentiated to definitive endoderm for three (3) days. Two (2) plates were treated with anti-human E-cadherin (Zymed Cat. No. 13-1700) at 5 μg/mL on the first day (d1). One plate did not receive anti-human E-cadherin (control). Six (6) plates were treated with anti-human E-cadherin (Zymed Cat. No. 13-5700) for the first (d1) or the first two (d1 and d2) days at concentration of 5, 1, or 0.2 μg/mL.

To determine cell surface marker expression, small samples of cells were harvested from differentiating plates, and total RNA was isolated from duplicate or triplicate samples with a 6100 nucleic acid extractor (Applied Biosystems) and 100-500 ng was used for reverse transcription with iScript cDNA synthesis kit (Bio-Rad). PCR reactions were run in duplicate using ¼0th of the cDNA per reaction and 400 nM forward and reverse primers with QuantiTect SYBR Green master mix (Qiagen). Alternatively, QuantiTect Primer Assays (Qiagen) were used according to the manufacturer's instructions. Real-time PCR was performed using the Rotor Gene 3000 (Corbett Research). Relative quantification was performed in relation to a standard curve. The standard curve was created using a mixture of total RNA samples from various fetal human endoderm tissues and differentiated hES cells, and 1 μg was used per cDNA reaction in creating the standard curve. Quantified values for each gene of interest were normalized against the input determined by two housekeeping genes (CYCG and GUSB or TBP). After normalization, the samples were plotted relative to the lowest detectable sample in the dataset and the standard deviation of four- or six-gene expression measurements was reported. Primer sequences: CXCR4 forward primer (5' to 3'), CACCG-CATCTGGAGAACCA (SEQ ID NO: 3); CXCR4 reverse primer (5' to 3'), GCCCATTTCCTCGGTGTAGTT (SEQ ID NO: 4); OCT4 forward primer (5' to 3'), TGGGCTC-GAGAAGGATGTG (SEQ ID NO: 5); OCT4 reverse primer (5' to 3'), GCATAGTCGCTGCTTGATCG (SEQ ID NO: 6); CER forward primer (5' to 3'), ACAACTACTTTTTCA-CAGCCTTCGT (SEQ ID NO: 7); CER reverse primer (5' to 3'), CCACGACTTGCCCAGCAT (SEQ ID NO: 8); NANOG forward primer (5' to 3'), GCAAATGTCTTCTGCT-GAGATGC (SEQ ID NO: 9); and NANOG Reverse primer (5' to 3'), CCATGGAGGAGGGAAGAGGA (SEQ ID NO: 10).

As can be seen in FIG. 3, the levels of cell surface marker expression were dependent on the dose of antibody provided. That is, levels of expression directly depended on the amount or concentration of anti-human E-cadherin added to the culture medium (e.g., 0.2, 1 and 5 μg/mL). For example, CXCR4 levels were increased at 3 days with antibody treatments at 1 μg/mL or 5 μg/mL of anti-human E-cadherin, whereas, samples treated with 0.2 μg/mL had CXCR4 expression levels substantially similar to those observed in the control samples (FIG. 3A). Another marker expressed in definitive endoderm is CERBERUS (CER). This marker was strongly upregulated after one day of E-cadherin antibody treatment and the upreguation was also dose-dependent (FIG. 3B).

Figure 3C:
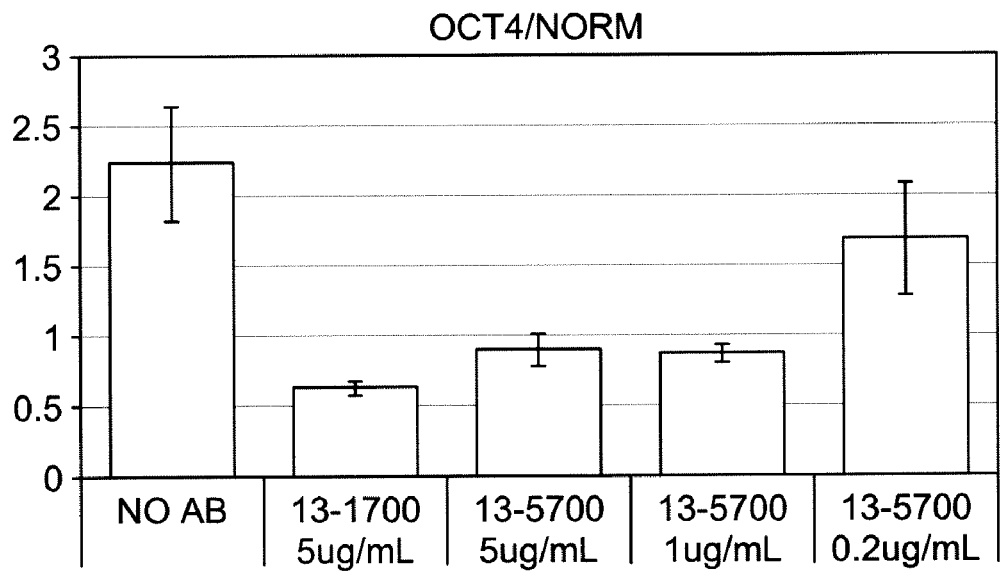
Figure 3D:
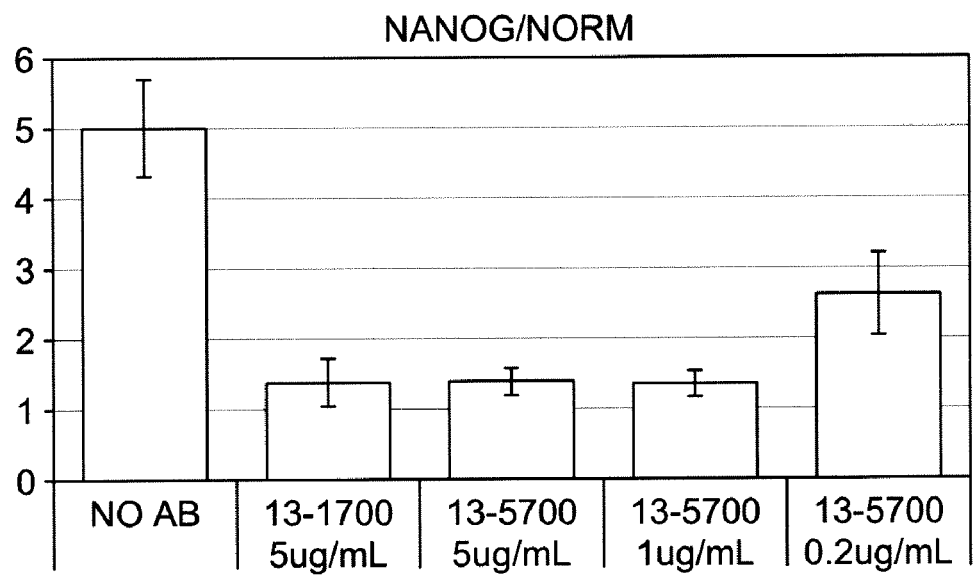

To determine the relative percentage of cells expressing Oct4 and Nanog, transcription factors required to maintain the hESC pluripotency and self-renewal, OCT4 and NANOG expression in the definitive endoderm cultures were analyzed. FIGS. 3C and 3D demonstrate that NANOG and OCT4 hESC expression levels were decreased with anti-human E-cadherin treatment, and at time periods typical of definitive endoderm formation (D'Amour et. al 2005, supra).

EXAMPLE 3

Figure 4:
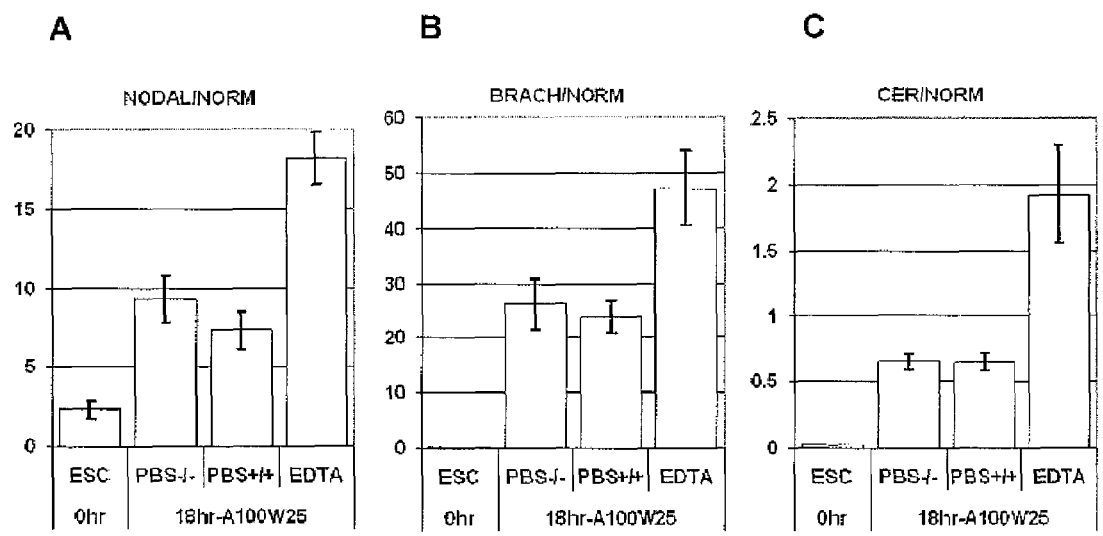
FIGS. 4A-C are bar charts showing the mRNA levels of certain markers as detected by QPCR in hESC derived cells that have been treated to differentiate to definitive endoderm cells along with treatment with EDTA. Specifically shown are the mRNA levels of NODAL (FIG. 4A), Brachyury (BRACH.

Decreased Levels of Extracellular Calcium Increases Production of Definitive Endoderm Cells Cell cultures and culture conditions were substantially similar to that described above and in D'Amour et al. 2005 and 2006 supra. Briefly, three 60 mm plates of hESCs (CyT203 p36) were differentiated for about 18 hr using activin A (100 ng/ml) and Wnt3a (25 ng/ml) in RPMI without FBS. Samples of undifferentiated hESCs were taken prior to the start of the differentiation procedure. Plates were briefly washed with 2 ml of PBS either containing $Ca^{2+}$ or $Mg^{2+}$ or without $Ca^{2+}$ and $Mg^{2+}$ (PBS$^{-/-}$). In addition, the one plate which was washed with PBS$^{-/-}$ also received ethylenediamine tetraacetic acid (EDTA) at 0.075 mM to reduce the concentration of $Ca^{2+}$ ions present in the media. Analysis by real-time PCR for expression of brachyury (BRACH), nodal (NODAL) and cerberus (CER) indicates that the addition of EDTA facilitated the differentiation to mesendoderm, as indicated by levels of BRACH (FIG. 4A) and NODAL (FIG. 4B), and definitive endoderm, as indicated by levels of CER (FIG. 4C). There was about a two-fold increase in gene expression for mesendoderm markers, and about a three-fold increase in expression for the DE marker in EDTA-treated cells. These data indicate that the reduction of extracellular calcium in the culture media in vitro was sufficient to increase efficient production of definitive endoderm from hESCs as compared to the no treatment control cultures.

In addition to EDTA, it will be appreciated that other calcium ion chelators can be used, including but not limited to, ethyleneglycoltetraacetic acid (EGTA), 1,10 phenanthroline, diethylenetriaminepentaacetate (DTPA), hydroxyethylethylenediaminetriacetic acid (HEEDTA), Diaminocyclohexanetetraacetic acid (CDTA), 1,2-Bis(2-aminophenoxy)ethane-N,N,N',N'-tetraacetic acid (BAPTA), and pharmaceutically acceptable salts thereof.

The methods and compositions described herein are presently representative of preferred embodiments and are exemplary and are not intended as limitations on the scope of the invention. Changes therein and other uses will occur to those skilled in the art which are encompassed within the spirit of the invention and are defined by the scope of the disclosure. Accordingly, it will be apparent to one skilled in the art that varying substitutions and modifications may be made to the invention disclosed herein without departing from the scope and spirit of the invention.

As used in the claims below and throughout this disclosure, by the phrase "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they affect the activity or action of the listed elements.

We claim:

1. An in vitro composition comprising a TGFβ superfamily growth factor and an antagonist of E-cadherin, said antagonist of E-cadherin bound to E-cadherin-expressing human embryonic stem cells, wherein the binding of the antagonist inhibits adhesion between said embryonic stem cells.

2. The composition of claim 1, wherein the antagonist is a polyclonal or a monoclonal E-cadherin antibody.

3. The composition of claim 1, wherein at least 10% of the human embryonic stem cells are not adhered to other human embryonic stem cells.

4. The composition of claim 1, wherein at least 50% of the human embryonic stem cells are not adhered to other human embryonic stem cells.

5. A cell culture comprising a TGFβ superfamily growth factor, a calcium-binding agent and E-cadherin-expressing human embryonic stem cells in a culture medium, wherein the calcium-binding agent is bound to calcium ions in the culture medium, thereby inhibiting adhesion between said embryonic stem cells.

6. The cell culture of claim 3, wherein the calcium binding agent is selected from the group consisting of ethylenediaminetetraacetic acid (EDTA), ethyleneglycoltetraacetic acid (EGTA), 1,10 phenanthroline, diethylenetriaminepentaacetate (DTPA), hydroxyethylethylenediaminetriacetic acid (HEEDTA), diaminocyclohexanetetraacetic acid (CDTA), 1,2-Bis(2-aminophenoxy)ethane-N,N,N',N'-tetraacetic acid (BAPTA), and pharmaceutically acceptable salts thereof.

7. The cell culture of claim 6, wherein at least 10% of the human embryonic stem cells are not adhered to other human embryonic stem cells.

8. The composition of claim 6, wherein at least 50% of the human embryonic stem cells are not adhered to other human embryonic stem cells.

9. The composition of claim 1, wherein said TGFβ superfamily growth factor comprises Activin A.

10. The composition of claim 1, wherein said TGFβ superfamily growth factor comprises Activin B.

11. The composition of claim 1, wherein said TGFβ superfamily growth factor comprises Nodal.

12. The composition of claim 1, wherein said composition further comprises human definitive endoderm cells.

13. The cell culture of claim 5, wherein said TGFβ superfamily growth factor comprises Activin A.

14. The cell culture of claim 5, wherein said TGFβ superfamily growth factor comprises Activin B.

15. The cell culture of claim 5, wherein said TGFβ superfamily growth factor comprises Nodal.

16. The cell culture of claim 5, wherein said cell culture further comprises human definitive endoderm cells.

17. The composition of claim 1, wherein said TGFβ superfamily growth factor comprises a member of the Nodal/Activin subgroup.

18. The composition of claim 1, wherein said TGFβ superfamily growth factor comprises a member of the BMP subgroup.

19. The cell culture of claim 5, wherein said TGFβ superfamily growth factor comprises a member of the Nodal/Activin subgroup.

20. The cell culture of claim 5, wherein said TGFβ superfamily growth factor comprises a member of the BMP subgroup.

* * * * *

UNITED STATES PATENT AND TRADEMARK OFFICE
CERTIFICATE OF CORRECTION

PATENT NO. : 7,695,963 B2
APPLICATION NO. : 11/860494
DATED : April 13, 2010
INVENTOR(S) : Alan Agulnick et al.

It is certified that error appears in the above-identified patent and that said Letters Patent is hereby corrected as shown below:

On (Item 56) Page 4, Col. 1, Line 58, under Other Publications, please change "Development" to --Developmental--;

On (Item 56) Page 5, Col. 1, Line 58, under Other Publications, please change "227; 238-245." to --227:238-245.--;

On Column 7, Line 19, please change "selecting." to --selectins.--;

On Column 8, Line 41, please change "interactions," to --interactions.--;

On Column 13, Line 47, please change "500 ng/ml" to --500 ng/ml,--;

On Column 16, Line 47, please change "thereof" to --thereof,--;

On Column 18, Line 62, please change "Biochem, Biophys.," to --Biochem. Biophys.--;

On Column 24, Line 49, please change "1:41:10" to --1:4—1:10--.

Signed and Sealed this

Thirtieth Day of November, 2010

David J. Kappos
*Director of the United States Patent and Trademark Office*

SEQUENCE LISTING

<160> NUMBER OF SEQ ID NOS: 10

<210> SEQ ID NO 1
<211> LENGTH: 882
<212> TYPE: PRT
<213> ORGANISM: Homo sapiens

<400> SEQUENCE: 1

Met Gly Pro Trp Ser Arg Ser Leu Ser Ala Leu Leu Leu Leu Leu Gln
1               5                   10                  15

Val Ser Ser Trp Leu Cys Gln Glu Pro Glu Pro Cys His Pro Gly Phe
            20                  25                  30

Asp Ala Glu Ser Tyr Thr Phe Thr Val Pro Arg Arg His Leu Glu Arg
        35                  40                  45

Gly Arg Val Leu Gly Arg Val Asn Phe Glu Asp Cys Thr Gly Arg Gln
    50                  55                  60

Arg Thr Ala Tyr Phe Ser Leu Asp Thr Arg Phe Lys Val Gly Thr Asp
65                  70                  75                  80

Gly Val Ile Thr Val Lys Arg Pro Leu Arg Phe His Asn Pro Gln Ile
                85                  90                  95

His Phe Leu Val Tyr Ala Trp Asp Ser Thr Tyr Arg Lys Phe Ser Thr
            100                 105                 110

Lys Val Thr Leu Asn Thr Val Gly His His His Arg Pro Pro Pro His
        115                 120                 125

Gln Ala Ser Val Ser Gly Ile Gln Ala Glu Leu Leu Thr Phe Pro Asn
    130                 135                 140

Ser Ser Pro Gly Leu Arg Arg Gln Lys Arg Asp Trp Val Ile Pro Pro
145                 150                 155                 160

Ile Ser Cys Pro Glu Asn Glu Lys Gly Pro Phe Pro Lys Asn Leu Val
                165                 170                 175

Gln Ile Lys Ser Asn Lys Asp Lys Glu Gly Lys Val Phe Tyr Ser Ile
            180                 185                 190

Thr Gly Gln Gly Ala Asp Thr Pro Pro Val Gly Val Phe Ile Ile Glu
        195                 200                 205

Arg Glu Thr Gly Trp Leu Lys Val Thr Glu Pro Leu Asp Arg Glu Arg
    210                 215                 220

Ile Ala Thr Tyr Thr Leu Phe Ser His Ala Val Ser Ser Asn Gly Asn
225                 230                 235                 240

Ala Val Glu Asp Pro Met Glu Ile Leu Ile Thr Val Thr Asp Gln Asn
                245                 250                 255

Asp Asn Lys Pro Glu Phe Thr Gln Glu Val Phe Lys Gly Ser Val Met
            260                 265                 270

-continued

```
Glu Gly Ala Leu Pro Gly Thr Ser Val Met Glu Val Thr Ala Thr Asp
        275                 280                 285
Ala Asp Asp Val Asn Thr Tyr Asn Ala Ala Ile Ala Tyr Thr Ile
    290                 295                 300
Leu Ser Gln Asp Pro Glu Leu Pro Asp Lys Asn Met Phe Thr Ile Asn
305                 310                 315                 320
Arg Asn Thr Gly Val Ile Ser Val Val Thr Thr Gly Leu Asp Arg Glu
                325                 330                 335
Ser Phe Pro Thr Tyr Thr Leu Val Val Gln Ala Ala Asp Leu Gln Gly
            340                 345                 350
Glu Gly Leu Ser Thr Thr Ala Thr Ala Val Ile Thr Val Thr Asp Thr
        355                 360                 365
Asn Asp Asn Pro Pro Ile Phe Asn Pro Thr Thr Tyr Lys Gly Gln Val
    370                 375                 380
Pro Glu Asn Glu Ala Asn Val Val Ile Thr Thr Leu Lys Val Thr Asp
385                 390                 395                 400
Ala Asp Ala Pro Asn Thr Pro Ala Trp Glu Ala Val Tyr Thr Ile Leu
                405                 410                 415
Asn Asp Asp Gly Gly Gln Phe Val Val Thr Thr Asn Pro Val Asn Asn
            420                 425                 430
Asp Gly Ile Leu Lys Thr Ala Lys Gly Leu Asp Phe Glu Ala Lys Gln
        435                 440                 445
Gln Tyr Ile Leu His Val Ala Val Thr Asn Val Val Pro Phe Glu Val
    450                 455                 460
Ser Leu Thr Thr Ser Thr Ala Thr Val Thr Val Asp Val Leu Asp Val
465                 470                 475                 480
Asn Glu Ala Pro Ile Phe Val Pro Pro Glu Lys Arg Val Glu Val Ser
                485                 490                 495
Glu Asp Phe Gly Val Gly Gln Glu Ile Thr Ser Tyr Thr Ala Gln Glu
            500                 505                 510
Pro Asp Thr Phe Met Glu Gln Lys Ile Thr Tyr Arg Ile Trp Arg Asp
        515                 520                 525
Thr Ala Asn Trp Leu Glu Ile Asn Pro Asp Thr Gly Ala Ile Ser Thr
    530                 535                 540
Arg Ala Glu Leu Asp Arg Glu Asp Phe Glu His Val Lys Asn Ser Thr
545                 550                 555                 560
Tyr Thr Ala Leu Ile Ile Ala Thr Asp Asn Gly Ser Pro Val Ala Thr
                565                 570                 575
Gly Thr Gly Thr Leu Leu Leu Ile Leu Ser Asp Val Asn Asp Asn Ala
            580                 585                 590
Pro Ile Pro Glu Pro Arg Thr Ile Phe Phe Cys Glu Arg Asn Pro Lys
        595                 600                 605
Pro Gln Val Ile Asn Ile Asp Ala Asp Leu Pro Pro Asn Thr Ser
    610                 615                 620
Pro Phe Thr Ala Glu Leu Thr His Gly Ala Ser Ala Asn Trp Thr Ile
625                 630                 635                 640
Gln Tyr Asn Asp Pro Thr Gln Glu Ser Ile Ile Leu Lys Pro Lys Met
                645                 650                 655
Ala Leu Glu Val Gly Asp Tyr Lys Ile Asn Leu Lys Leu Met Asp Asn
            660                 665                 670
Gln Asn Lys Asp Gln Val Thr Thr Leu Glu Val Ser Val Cys Asp Cys
        675                 680                 685
```

```
Glu Gly Ala Ala Gly Val Cys Arg Lys Ala Gln Pro Val Glu Ala Gly
    690                 695                 700
Leu Gln Ile Pro Ala Ile Leu Gly Ile Leu Gly Gly Ile Leu Ala Leu
705                 710                 715                 720
Leu Ile Leu Ile Leu Leu Leu Leu Phe Leu Arg Arg Arg Ala Val
                725                 730                 735
Val Lys Glu Pro Leu Leu Pro Pro Glu Asp Asp Thr Arg Asp Asn Val
                740                 745                 750
Tyr Tyr Tyr Asp Glu Glu Gly Gly Glu Glu Asp Gln Asp Phe Asp
            755                 760                 765
Leu Ser Gln Leu His Arg Gly Leu Asp Ala Arg Pro Glu Val Thr Arg
    770                 775                 780
Asn Asp Val Ala Pro Thr Leu Met Ser Val Pro Arg Tyr Leu Pro Arg
785                 790                 795                 800
Pro Ala Asn Pro Asp Glu Ile Gly Asn Phe Ile Asp Glu Asn Leu Lys
                805                 810                 815
Ala Ala Asp Thr Asp Pro Thr Ala Pro Pro Tyr Asp Ser Leu Leu Val
                820                 825                 830
Phe Asp Tyr Glu Gly Ser Gly Ser Glu Ala Ala Ser Leu Ser Ser Leu
            835                 840                 845
Asn Ser Ser Glu Ser Asp Lys Asp Gln Asp Tyr Asp Tyr Leu Asn Glu
    850                 855                 860
Trp Gly Asn Arg Phe Lys Lys Leu Ala Asp Met Tyr Gly Gly Gly Glu
865                 870                 875                 880
Asp Asp

<210> SEQ ID NO 2
<211> LENGTH: 13
<212> TYPE: PRT
<213> ORGANISM: Artificial Sequence
<220> FEATURE:
<223> OTHER INFORMATION: Synthetic Peptide

<400> SEQUENCE: 2

Ser Ala Leu Leu Leu Leu Leu Gln Val Ser Ser Trp Leu
1               5                   10

<210> SEQ ID NO 3
<211> LENGTH: 14
<212> TYPE: PRT
<213> ORGANISM: Artificial Sequence
<220> FEATURE:
<223> OTHER INFORMATION: Synthetic Peptide

<400> SEQUENCE: 3

Pro Gly Phe Asp Ala Glu Ser Tyr Thr Phe Thr Val Pro Arg
1               5                   10

<210> SEQ ID NO 4
<211> LENGTH: 19
<212> TYPE: DNA
<213> ORGANISM: Artificial Sequence
<220> FEATURE:
<223> OTHER INFORMATION: Primer

<400> SEQUENCE: 4
caccgcatct ggagaacca                                              19

<210> SEQ ID NO 5
<211> LENGTH: 19
```

```
<212> TYPE: DNA
<213> ORGANISM: Artificial Sequence
<220> FEATURE:
<223> OTHER INFORMATION: Primer

<400> SEQUENCE: 5
tgggctcgag aaggatgtg                                              19

<210> SEQ ID NO 6
<211> LENGTH: 20
<212> TYPE: DNA
<213> ORGANISM: Artificial Sequence
<220> FEATURE:
<223> OTHER INFORMATION: Primer

<400> SEQUENCE: 6
gcatagtcgc tgcttgatcg                                             20

<210> SEQ ID NO 7
<211> LENGTH: 25
<212> TYPE: DNA
<213> ORGANISM: Artificial Sequence
<220> FEATURE:
<223> OTHER INFORMATION: Primer

<400> SEQUENCE: 7
acaactactt tttcacagcc ttcgt                                       25

<210> SEQ ID NO 8
<211> LENGTH: 18
<212> TYPE: DNA
<213> ORGANISM: Artificial Sequence
<220> FEATURE:
<223> OTHER INFORMATION: Primer

<400> SEQUENCE: 8
ccacgacttg cccagcat                                               18

<210> SEQ ID NO 9
<211> LENGTH: 23
<212> TYPE: DNA
<213> ORGANISM: Artificial Sequence
<220> FEATURE:
<223> OTHER INFORMATION: Primer

<400> SEQUENCE: 9
gcaaatgtct tctgctgaga tgc                                         23

<210> SEQ ID NO 10
<211> LENGTH: 20
<212> TYPE: DNA
<213> ORGANISM: Artificial Sequence
<220> FEATURE:
<223> OTHER INFORMATION: Primer

<400> SEQUENCE: 10
ccatggagga gggaagagga                                             20
```